(12) United States Patent
Fathi et al.

(10) Patent No.: US 12,171,865 B2
(45) Date of Patent: Dec. 24, 2024

(54) BIOACTIVE POLYMER FOR BONE REGENERATION

(71) Applicant: Trimph IP Pty Ltd, Sydney (AU)

(72) Inventors: Ali Fathi, Northmead (AU); Fariba Dehghani, Killarney Heights (AU); Anthony Weiss, Randwick (AU); Suzanne Mithieux, Randwick (AU)

(73) Assignee: Trimph IP Pty Ltd, Sydney (AU)

( * ) Notice: Subject to any disclaimer, the term of this patent is extended or adjusted under 35 U.S.C. 154(b) by 988 days.

(21) Appl. No.: 17/090,078

(22) Filed: Nov. 5, 2020

(65) Prior Publication Data

US 2021/0093749 A1    Apr. 1, 2021

Related U.S. Application Data

(63) Continuation of application No. 15/753,556, filed as application No. PCT/AU2016/050817 on Aug. 31, 2016, now abandoned.

(30) Foreign Application Priority Data

Sep. 1, 2015    (AU) ................................ 2015903552

(51) Int. Cl.
| | | |
|---|---|---|
| *A61K 9/00* | (2006.01) | |
| *A61F 2/28* | (2006.01) | |
| *A61K 31/787* | (2006.01) | |
| *A61K 38/17* | (2006.01) | |
| *A61K 38/39* | (2006.01) | |
| *A61K 47/32* | (2006.01) | |
| *A61K 47/42* | (2017.01) | |
| *A61L 27/16* | (2006.01) | |
| *A61L 27/22* | (2006.01) | |
| *A61L 27/24* | (2006.01) | |
| *A61L 27/52* | (2006.01) | |
| *A61L 27/54* | (2006.01) | |
| *A61L 27/58* | (2006.01) | |
| *C08F 220/28* | (2006.01) | |
| *C08L 33/14* | (2006.01) | |
| *C08L 33/26* | (2006.01) | |
| *C08L 89/00* | (2006.01) | |

(52) U.S. Cl.
CPC .............. *A61K 9/0019* (2013.01); *A61F 2/28* (2013.01); *A61K 31/787* (2013.01); *A61K 38/1709* (2013.01); *A61K 38/39* (2013.01); *A61K 47/32* (2013.01); *A61K 47/42* (2013.01); *A61L 27/16* (2013.01); *A61L 27/227* (2013.01); *A61L 27/24* (2013.01); *A61L 27/52* (2013.01); *A61L 27/54* (2013.01); *A61L 27/58* (2013.01); *C08L 33/14* (2013.01); *C08L 33/26* (2013.01); *C08L 89/00* (2013.01); *A61F 2002/2817* (2013.01); *A61L 2300/252* (2013.01); *A61L 2300/412* (2013.01); *A61L 2400/06* (2013.01); *A61L 2430/02* (2013.01); *C08F 220/282* (2020.02); *C08F 220/285* (2020.02); *C08L 2201/06* (2013.01); *C08L 2201/54* (2013.01); *C08L 2203/02* (2013.01)

(58) Field of Classification Search
CPC .......... A61L 27/16; A61L 27/54; A61L 27/58; A61L 27/24; A61L 27/52; A61L 27/227; A61L 2400/06; A61L 2300/252; A61L 2430/02; A61L 2300/412; C08L 89/00; C08L 33/14; C08L 33/26; C08L 2201/06; C08L 2201/54; C08L 2203/02; A61F 2/28; A61F 2002/2817; A61K 9/0019; A61K 38/39; A61K 47/32; A61K 31/787; A61K 47/42; A61K 38/1709; C08F 220/285; C08F 220/282
See application file for complete search history.

(56) References Cited

U.S. PATENT DOCUMENTS

| | | |
|---|---|---|
| 8,283,384 B2 | 10/2012 | Stewart et al. |
| 9,272,069 B2 | 3/2016 | Stewart et al. |
| 9,546,235 B2 | 1/2017 | Dehghani et al. |
| 2010/0120923 A1 | 5/2010 | Stewart et al. |
| 2010/0305626 A1 | 12/2010 | Stewart et al. |
| 2013/0189313 A1 | 7/2013 | Stewart et al. |
| 2014/0357823 A1 | 12/2014 | Dehhani et al. |

(Continued)

FOREIGN PATENT DOCUMENTS

| | | | | |
|---|---|---|---|---|
| WO | WO-0170288 A2 | * | 9/2001 | ......... A61K 38/1875 |
| WO | WO 2004056321 | * | 7/2004 | |
| WO | 2013091001 A1 | | 6/2013 | |

(Continued)

OTHER PUBLICATIONS

Bahney et al., Bone Substitute Biomaterials, "9—Cartilage grafts for bone repair and regeneration", Abstract (Year: 2014).*

(Continued)

*Primary Examiner* — Lezah Roberts
(74) *Attorney, Agent, or Firm* — Amster, Rothstein & Ebenstein LLP

(57) ABSTRACT

Disclosed herein are biocompatible materials useful for tissue regeneration and repair, wherein the bioactive polymer may be in the form of a hydrogel, for example a thermoresponsive hydrogel. This bioactive polymer and a resulting hydrogel, may be used for the regeneration of bone tissue. Accordingly, also disclosed herein are methods of treating a bone defect in a mammal, the methods comprising administering a therapeutically effective amount of a hydrogel formed by the bioactive polymer to the mammal to treat the bone defect.

12 Claims, 14 Drawing Sheets

(56) References Cited

U.S. PATENT DOCUMENTS

2016/0058867 A1    3/2016    Kim et al.

FOREIGN PATENT DOCUMENTS

| WO | WO 2013091001 | * | 6/2013 |
|---|---|---|---|
| WO | 2014169045 A1 | | 10/2014 |
| WO | 2017015703 A1 | | 2/2017 |
| WO | 2017035595 A1 | | 3/2017 |

OTHER PUBLICATIONS

Elvira et al., "Free radical copolymerization of methyl methacrylate with methacrylic monomers derived from salicylic acid. Microstructural analysis, chain flexibility and hydration behaviour of the prepared copolymers", Polymer, 40, pp. 6911-6924 (Year: 1999).*

Australian Examination Report dated Nov. 26, 2019 from Australian Patent Appln. No. 2016314146.

Extended European Search Report dated Mar. 21, 2019 from European Patent Appln. No. 16840416.8.

Malavosklish et al., "Thermo-Responsive Systems for Controlled Drug Delivery," Expert Opin. Drug Deliv., Informa Healthcare GB, vol. 5, No. 10, 2008, pp. 1077-1091.

EPO Examination Report dated Jun. 9, 2020 from European Patent Appln. No. 16840416.8.

Japanese Office Action dated Jun. 9, 2020 from Japanese Patent Appln. No. 2018-529692 (with English language translation).

Communication Supplementary European Search Report dated Mar. 6, 2019 in connection with European Patent Application No. 16840416.8.

Bikram M et al., "Thermo-responsive systems for controlled drug delivery," Expert Opinion on Drug Deli, Informa Helathcare, GB, vol. 5, No. 10, Oct. 1, 2008, pp. 1077-1091.

PCT International Search Report and Written Opinion dated Oct. 18, 2016 in connection with PCT International Patent Application No. PCT/AU2016/050817, 10 pages.

Jabbari, E., 'Bone regeneration on proteolytically-degradable peptide-reinforced hydrogel nanocomposite', Chimica Oggi, 2007, vol. 25, No. 6, pp. 32-35.

Fathi, A. et al., 'Elastin based cell-laden injectable hydrogels with tunable gelation, mechanical and biodegradation properties', Biomaterials, 2014, vol. 35, pp. 5425-5435.

Chung, E. H. et al., 'Biomimetic artificial ECMs stimulate bone regeneration', Journal of Biomedical Materials Research Part A, 2006, vol. 79A, No. 4, pp. 815-826.

* cited by examiner

Mixed solution of Polymer and NSPP Flowable at 4 °C

37 °C

Gelation

BIOACTIVE POLYMER FOR BONE REGENERATION

CROSS-REFERENCE TO RELATED APPLICATIONS

This application is a continuation of U.S. patent application Ser. No. 15/753,556, filed Feb. 20, 2018, which is a U.S. national stage entry under 35 U.S.C. § 371 of PCT International Patent Application No. PCT/AU2016/050817, filed Aug. 31, 2016, which claims priority to Australian Provisional Patent Application No. 2015903552, filed Sep. 1, 2015, the contents of which are incorporated herein by reference in their entirety.

TECHNICAL FIELD

The present invention relates to a biocompatible material for tissue regeneration and repair. In particular, the invention relates to a bioactive polymer for regeneration of bone tissue. In one embodiment, the bioactive polymer is a hydrogel. In another embodiment, the hydrogel is thermoresponsive. In yet another embodiment, the polymers disclosed herein have been developed for delivery in an injectable form. However, it will be appreciated that the invention is not limited to this particular field of use.

BACKGROUND

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field, or that this prior art could reasonably be expected to be ascertained, understood and regarded as relevant by a person skilled in the art.

It is common knowledge that the body can efficiently repair fractures in bone. These small defects are often replaced by natural bone, which is even stronger than the original bone. Larger defects, however, generally cause more issues as the body is incapable of repairing them. Bone defects can occur as a result of congenital abnormalities, trauma, or disease. Bone is a very dense, specialised form of connective tissue, and the bone matrix consists of type I collagen and calcium phosphate in the form of hydroxyapatite. A compact, dense cortical layer comprises the outer region of long bones, while trabecular bone (cancellous bone) fills the interior. With the exception of articulating surfaces, cortical bone is surrounded by the thin connective tissue called periosteum, which consists primarily of a collagen-rich fibrous layer and osteoprogenitor cells.

Musculoskeletal injuries are among the most common work-related injuries in Australia, and impose an economic burden of approximately one billion dollars per year on the Australian economy, with an estimated 70% of the expenditure on long hospitalization services. This recovery period may exceed 12 to 16 weeks due to the slow rate of bone healing, and larger defects can take even longer to repair.

In another example, there are nearly 12,000 open cardiac surgeries in Australia per year, often with requisite rib or sternum fracture. In nearly 30% of minimally displaced complete fractures, closed or open reduction is required, which severely retards the natural healing process of the bone and thus delays full recovery. There is a need to accelerate the rate of bone healing in order to reduce the ancillary and associated hospitalization costs from work-related injuries and those arising from surgeries such open cardiac surgery.

In yet another example, in the US alone there are more than 8 million dental transplants each year, and the failure rate is nearly 30%. This high rate of failure is mainly due to the lack of primary stability in the implants and also bacterial infection after the surgery. The main focus in the past to address the problem of primary stability has been on the application of bone cements. However, uncontrollable and protracted setting reactions, and necrosis of bone cells at the implantation sites, are an issue. These effects lead to a low rate of osteoeintegration around the implants, dislocation of the metal segment, and ultimately the failure of the dental implant. Whilst there is a need for improvements in osteoeintegration, there is also a need for biomaterials that have adhesive properties and that can promote the regeneration of the bone around the dental implant. Additionally, the growth of soft tissue at the outer surface of the dental implant is also crucial to avoid the bacterial infection in the inner layers of the dental implant, and prior art dental fillers have been found to have little or no biological effect on the growth of soft tissue.

In cases where damage to bone is too severe to allow natural healing to take place, one option is to employ a bone graft to stimulate regeneration. Other options are to use 3D scaffolds that promote the migration, proliferation and differentiation of bone and endothelial cells. Such scaffolds are becoming increasingly important in not only orthopaedic but also maxillofacial surgery. An ideal bone replacement material should be mouldable, shapeable, or polymerisable in situ to ensure a good fit in the defect area. It should also support cellular adhesion and growth, maintain cellular differentiation, provide a porous matrix through which nutrients and wastes can easily diffuse, degrade in a controlled fashion into biocompatible by-products that the body can metabolise or excrete via normal physiological mechanisms, support bone formation and vascularisation, show minimal fibrotic reaction, and serve as a temporary biomaterial for bone remodelling. It is also crucial that these materials have mechanical properties similar to native bone, for example human trabecular bone typically has a compressive strength of 5 MPa and a modulus of 50 MPa. The material must maintain its mechanical properties as it degrades until the newly regenerated tissue can adequately support loading. If it fails mechanically, the material may lead to the failure of the patients arm or leg. On the other hand, if it is too strong, it may cause stress shielding of the remaining natural bone and result in bone erosion. Additionally, the surface of the implanted polymer will be immediately exposed to a physiological environment. In vivo, proteins will rapidly cover the surface of the material and tend to denature the surface. At present there are very few if any successful strategies available for bone tissue regeneration, which meet some or all of these requirements.

Over the last century, various materials have been investigated for the purpose of encouraging or stimulating bone growth and as scaffolds. For example, in the 1880s calcium sulfate (plaster of Paris) was utilised. However, calcium sulfate displays a relatively low bioactivity and a relatively high rate of degradation (Tay, et al., *Orthop. Clin. North Am.*, 1999, 30:615-23). In the 1950s hydroxyapatite was utilised, but it suffers from a relatively low degradation rate and poor mechanical properties (Wiltfang J., et al. *J. Biomed. Mater. Res.*, 2002; 63:115-21). In the 1970s Bioglass® was developed. However, this material it is relatively hard to handle due to its inherent brittleness and has a relatively low bending strength (Cordioli G., *Clin. Oral Implants Res.*, 2001, 13:655-65). In the 1990s calcium silicate ceramics began being used for stimulating bone growth. They are regarded as potential bioactive materials as their degradation products do not incite an inflammatory reaction. However, drawbacks exist with these materials that compromise their physical and biological properties, including:

a) inability to combine the required mechanical properties with open porosity;

b) poor mechanical strength making them unsuitable for load-bearing applications; and c) poor chemical instability (high degradation rate) leading to a highly alkaline condition in the surrounding environment which is detrimental to cell viability and limits their long-term biological applications.

Whilst other more recent ceramics such as HAp, Bioverit®, Ceraverit® and other calcium silicates have been found to bond to living bone and meet wide clinical applications, i.e., good bioactivity, they cannot be used in highly loaded areas, such as the cortical bone found in, for example, legs, due to the relative brittleness of these materials. However, their high compression strength justifies their use in the treatment of calcaneal fractures, augmentation of osteoporotic fractures and for certain spinal injuries. Despite some promising outcomes in the use of these fillers to treat orthopaedic injuries, their applications suffer from significant technical limitations, which can lead to prolonged recovery periods. These issues include:

(1) necrosis at the filling site and leakage to the surrounding tissues due to the uncontrollable (increase of temperature at the tissue border up to 80° C.) and protracted (completion after 24 hours post-surgery) curing reaction; and (2) their incomplete bioresorption (even after 12 months post-surgery) which leads to long term clinical complications.

Thus these materials possess good bioactivity, but lack full biodegradability after implantation, and their mechanical strength is compromised; they are too brittle and fracture frequently. For at least these reasons such materials typically find their use limited to coatings on metallic implants.

Synthetic scaffolds, such as hydrogels, offer better control of the matrix architecture and chemical composition. However, a number of limitations apply to the use of hydrogels that consist of synthetic molecules. First, hydrogels are formed from polymers that must initially be crosslinked before the hydrogel can form. Crosslinking is an additional manufacturing step that increases likelihood of contamination of the hydrogel, particularly with toxic components, or otherwise decreases the likelihood of biocompatibility with tissue. Secondly, synthetic hydrogels have low biological activities and therefore are limited in the extent to which they can provide a substrate for interaction with biological elements. In particular, hydrogels typically suffer from a lack of osteoconductive properties.

There is a need for improved hydrogels that effectively model the shape, strength and resilience characteristics of bone.

There is a need for synthetic hydrogels that can be formed without the use of chemical crosslinking, or crosslinking by UV irradiation or the like, and which do not damage surrounding bone tissue and also are applicable for deep tissue regeneration. This is because the use of UV limits the depth at which hydrogels can be administered and subsequently crosslinked.

There is also a need for hydrogels that bind to growth factors, drugs and the like, and that are a useful substrate for growth of cells thereon/therein, especially osteoblasts.

There is also a need for compositions for repair of bone that are injectable at room temperature and that form a hydrogel at body temperature.

Additionally, there is a need for improved biomaterials which are injectable and osteogenic and act as an adhesive elastic glue at the incision site and (a) promotes a rapid healing rate of the defect bone and (b) diminishes the risk of bone displacement.

It is a preferred aim of the present invention to overcome or ameliorate at least one of the disadvantages of the above mentioned prior art, or to provide a useful alternative.

Although the invention will be described with reference to specific examples it will be appreciated by those skilled in the art that the invention may be embodied in many other forms.

SUMMARY

According to a first aspect, provided herein is the use of a polymer for repairing or restoring bone, the polymer comprising:

a first monomer for binding water;

a second monomer for imparting mechanical properties to a hydrogel; and a third monomer for binding to a natural or synthetic protein or peptide (NSPP), wherein the polymer is introduced to bone to be regenerated or repaired.

In certain embodiments, the polymer further includes:

a fourth monomer for imparting phase transition characteristics to a hydrogel enabling injection at room temperature, and gel formation at body temperature.

It will be appreciated that each of the monomers are selected or are adapted for the intended purpose. For example, the first monomer is selected such that it binds water, or is adapted such that it binds water. The second monomer is selected for, or is adapted to, impart mechanical properties to the hydrogel. The third monomer is selected for, or is adapted to, bind to a NSPP. The fourth monomer is selected for, or is adapted impart phase transition characteristics to the hydrogel.

In one embodiment the fourth monomer has a lower critical solution temperature less than about 33° C. For example the LCST may be about 33° C., about 32° C., about 31° C., or about 30° C.

It will be appreciated by a person skilled in the art that the temperature responsiveness is from the fourth monomer. However, the exact LCST temperature is dictated by a number of factors, including the ratio of hydrophilic to hydrophobic moieties within the final polymer. For example, higher amounts of a hydrophobic monomer (such as a hydrophobic second monomer), can result in lower LCST values. The LCST will be raised in polymers where the hydrophobic/hydrophilic ratio favours hydrophilic characteristics.

In one embodiment the proportion of the first monomer in the polymer is in a range of about 4 to 15 mol %. For example the first monomer may be present in an amount of: about 4, about 5, about 6, about 7, about 8, about 9, about 10, about 11, about 12, about 13, about 14, or about 15 mol %.

In one embodiment the proportion of the second monomer in the polymer is in a range of about 2 to 15 mol %. For example the second monomer may be present in an amount of: about 2, about 3, about 4, about 5, about 6, about 7, about 8, about 9, about 10, about 11, about 12, about 13, about 14, or about 15 mol %.

In one embodiment the proportion of third monomer in the polymer is in a range of about 1 to 20 mol %. For example the third monomer may be present in an amount of: about 1, about 2, about 3, about 4, about 5, about 6, about 7, about 8, about 9, about 10, about 11, about 12, about 13, about 14, about 15, about 16, about 17, about 18, about 19, or about 20 mol %.

In another embodiment the proportion of fourth monomer in the polymer is in a range of about 60 to 90 mol %. For example the fourth monomer may be present in an amount of: about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, or about 90 mol %.

According to a second aspect, provided herein is use of a composition for forming a hydrogel for the repair or restoration of bone. The composition comprises:
   a natural or synthetic protein or peptide (NSPP); and
   a polymer,
wherein the polymer includes:
   a first monomer for binding water; and
   a second monomer that is bindable to the NSPP,
wherein the binding of the NSPP to the second monomer crosslinks the polymer, thereby enabling formation of a hydrogel when the composition is contacted with water, wherein the composition is introduced to bone to be regenerated or repaired.
   In certain embodiments, the polymer further includes:
   a third monomer for imparting mechanical properties to a hydrogel.
This third monomer enables the polymer to contribute additional mechanical properties (such as strength and resilience) to the hydrogel.
   In additional embodiments, the polymer further includes:
   a fourth monomer for imparting phase transition characteristics to a hydrogel enabling injection at room temperature, and gel formation at body temperature.

According to a third aspect, provided herein is use of a hydrogel for repairing or restoring bone comprising:
   water;
   a natural or synthetic protein or peptide (NSPP); and
   a polymer;
wherein the polymer includes:
   a first monomer for binding water; and
   a second monomer that is bindable to the NSPP,
wherein the binding of the NSPP to the second monomer crosslinks the polymer, thereby forming the hydrogel.
   In certain embodiments, the polymer further includes:
   a third monomer for imparting mechanical properties to a hydrogel.
As disclosed previously, the incorporation of this third monomer enables the polymer to contribute additional mechanical properties (such as strength and resilience) to the hydrogel.
   In additional embodiments, the polymer further includes:
   a fourth monomer for imparting phase transition characteristics to a hydrogel enabling injection at room temperature, and gel formation at body temperature.

According to a fourth aspect, provided herein is a polymer for forming a hydrogel, the polymer comprising:
   a first monomer for binding water;
   a second monomer for imparting mechanical properties to said hydrogel; and
   a third monomer for binding to a natural or synthetic peptide or protein (NSPP),
wherein the polymer is used to repair or restore bone.

According to a fifth aspect, provided herein is a composition for forming a hydrogel, the composition comprising:
   a natural or synthetic peptide or protein (NSPP); and
   a polymer,
wherein the polymer includes:
   a first monomer for binding water; and
   a second monomer that is bindable to said NSPP,
wherein:
   the binding of said NSPP to the second monomer crosslinks the polymer, thereby enabling formation of said hydrogel when the composition is contacted with water; and
   the composition is used to repair or restore bone.

According to a sixth aspect, provided herein is a hydrogel comprising:
   a natural or synthetic peptide or protein (NSPP); and
   a polymer,
wherein the polymer includes:
   a first monomer for binding water; and
   a second monomer that is bindable to said NSPP,
wherein:
   the binding of said NSPP to the second monomer crosslinks the polymer in the presence of water; and
   the hydrogel is used to repair or restore bone.

According to a seventh aspect, provided herein is a method of treatment of a bone defect in a mammal, the method comprising the steps of introducing or administering a therapeutically effective amount of a polymer to said bone defect site thereby to repair or restore said bone, the polymer comprising:
   a first monomer for binding water;
   a second monomer for imparting mechanical properties to said hydrogel; and
   a third monomer for binding to a natural or synthetic peptide or protein (NSPP).

According to an eighth aspect, provided herein is a method of treatment of a bone defect in a mammal, the method comprising the steps of introducing or administering a therapeutically effective amount of the composition that forms a hydrogel to the mammal to said bone defect site thereby to repair or restore said bone, the composition comprising:
   a natural or synthetic peptide or protein (NSPP); and
   a polymer;
wherein the polymer includes:
   a first monomer for binding water; and
   a second monomer that is bindable to said NSPP,
wherein the binding of said NSPP to the second monomer crosslinks the polymer, thereby enabling formation of said hydrogel when the composition is contacted with water.

According to a ninth aspect, provided herein is a method of treatment of a bone defect in a mammal, the method comprising the step of introducing or administering a therapeutically effective amount of a hydrogel to the mammal to said bone defect site thereby to repair or restore said bone, the hydrogel comprising:
   a natural or synthetic peptide or protein (NSPP); and
   a polymer;
wherein the polymer includes:
   a first monomer for binding water; and
   a second monomer that is bindable to said NSPP, wherein the binding of said NSPP to the second monomer crosslinks the polymer in the presence of water.

It will be appreciated that the steps of repairing or restoring bone are taken to additionally comprise the steps of regenerating and/or resurfacing and/or stabilising bone. It will also be appreciated that the polymer, composition or hydrogel as disclosed herein are taken to be medicaments for the treatment of bone degeneration conditions that require the repair, restoration, regeneration or resurfacing of bone at a target bone injury or defect site.

According to a tenth aspect, provided herein is a kit, comprising:
polymer;
wherein the polymer includes:
  a first monomer for binding water; and
  a second monomer that is bindable to a natural or synthetic protein or peptide (NSPP)

The kit according to the tenth aspect optionally further comprising water in a separate container.

According to an eleventh aspect, provided herein is a kit, including in separate containers:
  a NSPP; and
  a polymer,
wherein the polymer includes:
  a first monomer for binding water; and
  a second monomer that is bindable to the NSPP,
wherein the binding of the NSPP to the second monomer crosslinks the polymer, thereby enabling formation of a hydrogel when the composition is contacted with water.

In certain embodiments, the polymer further includes:
  a third monomer for imparting mechanical properties to a hydrogel.

This third monomer enables the polymer to contribute additional mechanical properties (such as strength and resilience) to the hydrogel. In additional embodiments, the polymer further includes:
  a fourth monomer for imparting phase transition characteristics to a hydrogel enabling injection at room temperature, and gel formation at body temperature.

Preferably the kit includes instructions for the sequential or simultaneous administration of its components.

According to a twelfth aspect, provided herein is a method of surgery comprising the steps of administering to a bone defect site a polymer, composition or hydrogel as disclosed herein for the treatment of a bone degeneration condition.

The present invention provides the kits of the tenth or eleventh aspects when used to treat a bone defect in a mammal.

Definitions

In describing and claiming the present invention, the following terminology will be used in accordance with the definitions set out below. It is also to be understood that the terminology used herein is for the purpose of describing particular embodiments of the invention only and is not intended to be limiting. Unless defined otherwise, all technical and scientific terms used herein have the same meaning as commonly understood by one having ordinary skill in the art to which the invention pertains.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

As used herein a wording defining the limits of a range or length such as, for example, "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, an "implant" refers to an article or device that is placed entirely or partially into an animal, for example by a surgical procedure. The animal may be a human, a horse, a cow, pig, sheep, etc.

As used herein, the term "natural or synthetic peptide or protein" (or NSPP) refers to proteins or peptides that are naturally present in the extracellular part of animal tissue that provides structural support to the animal cells (in addition to performing various other important functions). The term also refers to synthetically prepared proteins or peptides which have analogous function to those naturally-occurring proteins and peptides. By way of example naturally-occurring proteins and peptides are those commonly found in the extracellular matrix (or ECM), which is the defining feature of connective tissue in animals. Naturally-occurring proteins commonly found in the ECM include collagen, fibrin, fibronectin, and laminin (and isoforms thereof). Preferred NSPPs are: collagen, bone morphogenic natural proteins and bone morphogenic synthetic proteins, and synthetic peptides. Not included the NSPPs contemplated in the present invention are: α-elastin, β-elastin, animal-derived elastin or tropoelastin in any form.

Other than in the operating examples, or where otherwise indicated, all numbers expressing quantities of ingredients or reaction conditions used herein are to be understood as modified in all instances by the term "about". The examples are not intended to limit the scope of the invention. In what follows, or where otherwise indicated, "%" will mean "weight %", "ratio" will mean "weight ratio" and "parts" will mean "weight parts".

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

BRIEF DESCRIPTION OF DRAWINGS

Preferred embodiments of the invention will now be described, by way of example only, with reference to the accompanying figures.

DESCRIPTION OF EMBODIMENTS

Figure 1:
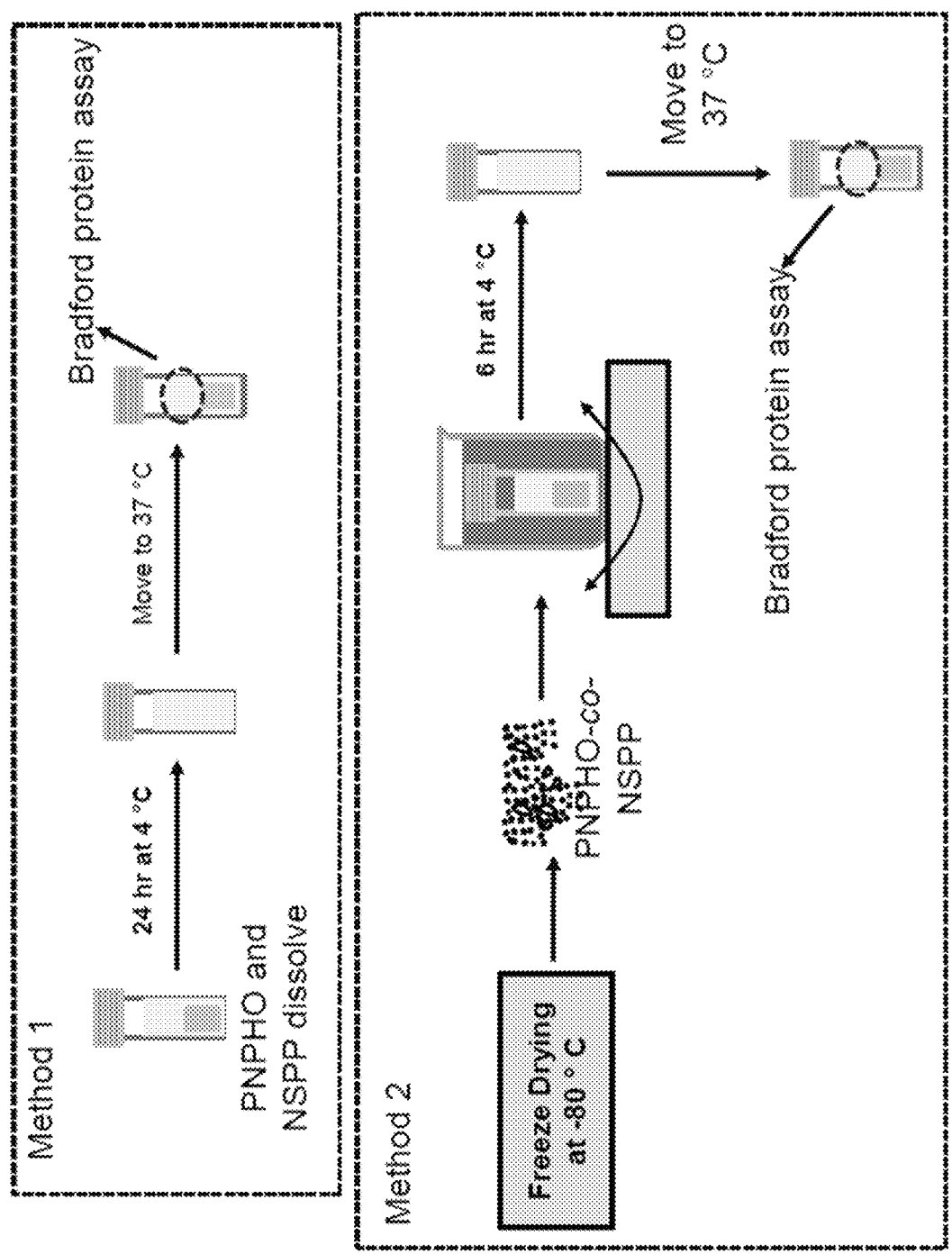
FIG. 1: Different methods for conjugation of NSPP and PNPHO for formation of NSPP-PNPHO hydrogels.

The present invention will now be more fully described with reference to the accompanying examples and drawings. It should be understood, however, that the description following is illustrative only and should not be taken in any way as a restriction on the generality of the invention described above.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

Disclosed herein is the use of a polymer that is tailored for bone repair. The polymer is preferably a hydrogel, and is preferably injectable. Further, the polymer is preferably thermoresponsive in the respect that it is thermosetting at body temperatures via a benign crosslinking reaction which does not damage surrounding tissue. Preferably the polymer provides a 3D scaffold that promotes the migration, proliferation and differentiation of bone and endothelial cells. Preferably the polymer promotes a rapid healing rate of the defect bone via support of the growth of osteoblasts within its structure, is osteogenic, and diminishes the risk of bone displacement. Preferably the polymer is mechanically strong and elastic. Preferably the polymer provides a porous matrix through which nutrients and wastes can easily diffuse. Preferably the polymer degrades in a controlled fashion into biocompatible by-products that the body can metabolise or excrete via normal physiological mechanisms, supports bone formation and vascularisation, shows minimal fibrotic reaction, and serves as a temporary biomaterial for bone remodelling. Preferably the polymer has mechanical properties similar to native bone, and maintains its mechanical properties as it degrades until the newly regenerated tissue can adequately support loading. The present invention provides the use of an elastic polymer in bone repair, which is an advance over the prior art which uses stiff materials.

The full potential of a cellular injectable hydrogels for bone regeneration has not yet been adequately explored due to their intrinsic low mechanical strength and lack of osteoconductive properties. The present invention details the use of specific (co)polymers (hydrogels) which are thermoresponsive and injectable with tunable physicochemical properties for the regeneration of bone. This copolymer discussed herein can be covalently bonded with a variety of different natural or synthetic proteins or peptides (NSPPs). These NSPPs may be selected from the group consisting of: collagen, bone morphogenic natural proteins and bone morphogenic synthetic proteins, and natural or synthetic peptides. Combinations of natural and synthetic proteins and peptides are contemplated by the present invention. Examples of natural peptides are: collagen monomer peptides and fibrin. Examples of synthetic peptides are: different Arg-Gly-Asp-Ser (RGDS), and synthetic bone morphogen peptides. The polymer-NSPP precursor solutions are injectable and exhibit high compression strength, tissue adhesive properties, and osteoconductive properties. These properties enable their potential for bone regeneration applications, and they can be used as an adhesive material in non-invasive surgeries. In particular, the polymers described herein can be used as a first treatment strategy to fill a bone gap and to keep the bone fractures intact and in place to ultimately prevent the need for open surgeries.

A preferred final product is a co-polymer (PNPHO-NSPP) which can be dissolved in biologically compatible isotonic buffer (PBS) and directly injected to the bone fracture site. This biomaterial brings significant changes in orthopaedic surgery as a non-invasive treatment:
  (i) to adhere to the bone surface to keep the bone aligned in comminuted fractures; and
  (ii) to fill the gap at the fracture site to promote the bone formation.

The present inventors have found that the hydrogel polymer disclosed herein is surprisingly useful for repair of bone. A skilled person would understand that cartilage is very different to bone in terms of structure and composition of the matrix, and methods in the art which are suited to treating or repairing one are not suitable for the other. Key considerations in the design of the polymer have been to ensure that:
  (i) all components of the hydrogel can be delivered from external sources and without reliance on cell or tissue machinery;
  (ii) the components, in particular the NSPP(s) are bound so that they do not dissociate in vivo;
  (iii) chemical and UV crosslinking is not required;
  (iv) the hydrogel is injectable at room temperature; and
  (v) the hydrogel is a compatible substrate for bone cells and bone tissue.

Preferably the polymer comprises a monomer having a functional group for binding to a NSPP into a synthetic polymer, thereby enabling the NSPP to crosslink the polymer for formation of hydrogel scaffolds that can be used for tissue engineering, and in particular in bone repair and regeneration. The preferred hydrogels are formed by combining an NSPP (e.g. collagen) with a hydrophilic polymer that is capable of binding to the NSPP. Therefore, the preferred hydrogels can be formed without the use of any additional agents (e.g. crosslinking initiators) or special conditions (e.g. irradiation of the polymers with UV and/or IR radiation) to effect the crosslinking of the polymers, while still providing a scaffold that can be used to encapsulate cells and other NSPP components to assist in bone repair and regeneration, upon administration of the hydrogel to the desired site. The preferred hydrogels also have the added advantage of being easily administrable (e.g. via injection) directly to the desired site, due to its phase-transition properties.

The advantageous properties of the preferred hydrogels can be attributed to the combination of a NSPP and the particular components of the polymer. In particular, the preferred polymers used with invention possess the required water-binding capacity and crosslinking ability (which can also be referred to as conjugation ability), such that they are able to bind to NSPPs and form hydrogels containing the NSPPs, in addition to having, in some embodiments, particular components that contribute to the strength, shape, resilience and phase-transfer properties of the hydrogel, once formed. The NSPP, in addition to providing an environment that mimics, to some extent, the natural environment of the bone tissue to be replaced and/or repaired, also provide the requisite strength and shape to the hydrogels of the present invention. This is particularly important in applications such as bone repair and replacement, where hydrogels need to withstand the stresses commonly placed on bone.

Polymers useful for the present invention are those having the desired characteristics for use in hydrogels intended for bone tissue repair, and in particular those hydrogels intended for repair and/or replacement of bone, by combining components that either inherently possess some of these characteristics, or that can provide such characteristics to the hydrogel once it is formed. Accordingly, preferred polymers include, within their structure, particular units (e.g. monomers, macromonomers, and the like) that have been chosen based on their ability to convey the desired water-binding, crosslinking, strength, resilience and phase-transfer properties to the hydrogels formed from such polymers. In addition, the properties of these polymers (and therefore the hydrogels formed from these polymers) can be tuned, in the sense that different monomers, as well as different proportions of these monomers, can be selectively incorporated into the polymers.

These advantageous properties of the preferred hydrogels are discussed throughout the present specification, and in particular, are exhibited in the Examples, which show that preferred hydrogels for use with the present invention can be made in a relatively simple manner using a relatively simple combination with NSPPs, and that the hydrogels thus formed possess the required properties of strength, resilience and shape, that enables them to be used in bone tissue engineering applications.

Also disclosed herein is the administration of the polymer, composition, or hydrogel (as defined herein), to an endosteum region by micro-drilling or oscillating saw of cortical bone or to an osteotomy site.

A. Polymers

The term "polymer", as used herein, refers to a large molecule (macromolecule) composed of repeating structural units (monomers). These subunits are typically connected by covalent chemical bonds. Polymers can be linear or branched polymers. Preferably, the polymers of the present invention are copolymers comprising three or more different monomers.

Accordingly, in one embodiment, preferred polymers used herein include a first water-binding monomer, a second monomer that is capable of imparting mechanical properties to a hydrogel, and a third monomer that has a functional group for binding to a NSPP.

The term "monomer", as used herein, refers to a structural unit that can be combined to form a polymer, but that itself may also be a polymer, or a derivative of a monomer or polymer. Monomers of this latter type are herein also referred to as "macromonomers".

Herein a "macromonomer" is a polymer or oligomer the molecules of which each have one end-group that acts as a monomer molecule, so that each polymer or oligomer molecule contributes only a single monomer unit to a chain of the product polymer.

A1. Water-Binding Monomers

As discussed above, the advantageous properties of the preferred hydrogels used herein can be attributed to the combination of a NSPP and the particular components of the preferred polymers. One particular advantageous property of these preferred polymers is their water-binding capacity. The presence of water in the hydrogels provides both an environment that resembles the natural environment of the damaged tissue (which assists in tissue regeneration), and the required compression resistance to the hydrogel.

Accordingly, the preferred polymers used herein should include monomers or units that are able to bind water to such a capacity that a hydrogel is able to form when the polymer is contacted with an NSPP and water. In addition, the hydrogel thus formed should have the required compression resistance and resilience. This is important for bone repair and restoration, because, as discussed above, bone is commonly subjected to significant mechanical stresses.

A person skilled in the art will understand that water-binding monomers need to be present in the preferred polymers used in the present invention in proportions that are sufficient to produce a polymer that fulfils these requirements. Generally, the proportion of water binding monomers in the polymer may be: about 10:1, about 5:1, about 4:1, about 3:1, about 2:1, about 1:1, about 1:2, about 1:3, about 1:4, or about 1:5 in a molar ratio of water binding:mechanical strength monomers. In fact, the water-binding monomers need to make the polymer not only hydrophilic, but impart much more significant water-binding capacities to the polymer. Accordingly, preferred polymers to be used in the present invention will have water-binding capacities of between about 70% and about 500%, between about 80% and about 400%, between about 90% and 300% or between about 100% and 200%. For example, the water-binding capacity of the preferred polymers used herein is about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500%.

Suitable examples of water-binding monomers include those that can be synthesised into polymers such as polyethers (e.g., alkaline polyimides such as polyethylene glycol (PEG), oligo(ethylene glycol) (OEG), polyethylene oxide (PEO), polyethylene oxide-co-propylene oxide (PPO), co-polyethylene oxide block or random copolymers, polyvinyl alcohol (PVA), poly(vinyl pyrrolidone) (PVP), poly (amino acids) and dextran. The polyethers, and more particularly oligo(oxyalkylenes) (e.g. OEG), are especially preferred, because they have the requisite water-binding capacity, are simple to synthesise and/or purchase, and are inert, in the sense that they illicit minimal or no immune response from the tissues into which they are placed.

In addition, any of a variety of hydrophilic functionalities can be used to make a monomer (and therefore a polymer formed from such a monomer) water soluble. For example, functional groups like phosphate, sulphate, quaternary amine, hydroxyl, amine, sulfonate and carboxylate, which are water soluble, may be incorporated into a monomer to make it water soluble.

A2. Imparting Mechanical Properties

As discussed above, the advantageous properties of the preferred hydrogels used with the present invention can be attributed, in part, to the particular components that make up the polymers. In some embodiments, the preferred polymers used in the present invention are able to contribute additional mechanical properties to the hydrogels, which produces hydrogels that, due to their strength and resilience, can be used in the repair and restoration of bone tissue.

Accordingly, the preferred polymers used within the present invention may include monomers or units that are able to provide strength and resilience required in bone repair and restoration.

A person skilled in the art will understand that monomers capable of imparting mechanical properties to a hydrogel need to be present in the preferred polymers in proportions that are sufficient to produce a hydrogel having the desired mechanical properties. Generally, the proportion of "mechanical" monomers in the polymer may be: about 10:1, about 5:1, about 4:1, about 3:1, about 2:1, about 1:1, about 1:2, about 1:3, about 1:4, or about 1:5 in a molar ratio of water binding:mechanical strength monomers. Suitable examples of monomers that are capable of imparting mechanical properties (e.g. compression resistance) to a hydrogel include methacrylates such as hydroxyethyl methacrylate (HEMA), a hydroxyethyl methacrylate poly(lactic acid) copolymer (HEMA-PLA), polyesters such as poly (lactic acid), poly(caprolactone), poly(glycolide), and their random co-polymers (e.g. poly(glycolide-co-lactide) and poly(glycolide-co-caprolactone)).

A3. NSPP Binding

As discussed above, the preferred hydrogels used in the present invention form by combining the polymer with a NSPP, in the presence of water. In order to effectively combine the polymer with the NSPP, preferably monomers or units that have a crosslinking ability are included in the polymer.

This crosslinking ability means that the polymers are able to bind to NSPPs (as discussed further below) and, by doing so, crosslink the NSPP to form hydrogels containing the NSPP. Alternatively, via a similar mechanism, the NSPPs act as the crosslinker, thereby crosslinking the polymer to form a hydrogel.

By utilising a polymer design whereby a monomer having a functional group for binding with collagen or the like is provided in the polymer, the inventors have recognised that polymers do not need to be further crosslinked with, for example, chemical or UV crosslinking, to form a hydrogel.

In addition, by covalently binding the NSPP to the polymer, the NSPP is more effectively retained in the hydrogel network, which means that, once the hydrogel is administered to the repair site, the NSPP is not able to migrate easily away from the site. This means that the structural integrity of the gel at the repair site is maintained (due to the mechanical properties of NSPPs, as mentioned above), and assists in providing an environment at the repair site that closely mimics the natural environment of the bone tissue.

In order to produce a polymer that is capable of binding to a NSPP, a person skilled in the art will understand that monomers capable of binding to a NSPP need to be present in the polymers of the present invention in proportions that are sufficient to crosslink with a NSPP, such that a hydrogel can be formed in the presence of water. Generally, the proportion of "crosslinking" monomers in the polymer is at least about 1:1 molar ratio of crosslinking monomer:water binding monomer. This ratio can increase to, for example, about 2:1, about 3:1, about 4:1, about 5:1, about 6:1, about 7:1, about 8:1, about 9:1 or about 10:1.

Monomers that are capable of binding to NSPPs generally have either electrophilic or nucleophilic functional groups, such that a nucleophilic functional group on, for example, an NSPP may react with an electrophilic functional group on the monomer, to form a covalent bond. Preferably, the polymer comprises more than two NSPP-binding monomers, so that, as a result of electrophilic-nucleophilic reactions, the polymer combines with the NSPP to form crosslinked polymeric products. Such reactions are referred to as "crosslinking reactions".

Therefore, for example, if a NSPP has nucleophilic functional groups such as amines, the polymer may have electrophilic functional groups such as N-hydroxysuccinimides (NHS). Other electrophilic functional groups that are suitable for use in the present invention are N-hydroxysulfosuccinimide (SNHS) and N-hydroxyethoxylated succinimide (ENHS). An example of a monomer of this type is N-acryloxysuccinimide (NAS). On the other hand, if an NSPP has electrophilic functional groups, then the polymer may have nucleophilic functional groups such as amines or thiols.

A4. Phase-Transition Monomers

In another embodiment, the preferred polymer may further include a fourth monomer that is capable of imparting phase transition characteristics to the hydrogel, thereby enabling the composite to be in an injectable form at room temperature, and in a hydrogel form at body temperature. Further, these phase transition characteristics allow the preferred polymers used with the present invention to form hydrogels, of which various properties (such as viscosity) can be varied by altering factors such as pH and temperature. Thermo-responsive injectable hydrogels are designed such that the lower critical solution temperature (LCST) is below body temperature. Therefore, gelation can be achieved simply by increasing the temperature of the hydrogel by, for example, letting it warm up to body temperature (which occurs when the hydrogel is administered into the body). Various thermo-responsive and injectable polymers including poly(ethylene oxide)/poly(propylene oxide) and poly(N-isopropylacrylamide) (PNIPAAm) homopolymers and copolymers are suitable for use in the present invention. PNIPAAm is particularly suitable, as it has a LCST of 32° C., allowing it to be in the gel form at body temperature.

In order to produce a polymer that is thermoresponsive, a person skilled in the art will understand that the phase-transition monomers need to be present in the polymers used with the present invention in proportions that are sufficient to enable the viscosity of a hydrogel including the polymer to be varied by exposure of the hydrogel to different conditions of temperature and pH. Generally, the proportion of "phase-transition" monomers in the polymer is at least about 9:1 molar ratio of phase-transition monomer:water binding monomer. This ratio can increase to, for example: about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, or about 30:1 in a molar ratio of phase-transition monomer: water binding monomer.

The viscosity of the preferred hydrogels used with the present invention, at lower temperatures (e.g. 4° C.), is such that the hydrogel is injectable. The hydrogel then becomes more viscous as the temperature increases, forming a gel having the desired viscosity at a temperature of about 37° C. This means that the preferred hydrogel used with the present invention, at cooler temperatures, can be administered easily to the site of repair by, for example, injection. The hydrogel is then transformed, by warming in the body to the body's natural temperature, into a more viscous gel, which has the desired strength and elasticity properties.

A5. Other Polymer Properties and Synthesis of Polymers

It will be understood by a person skilled in the art that, by combining different types of monomers, polymers can be produced that have a range of different properties. In addition, by incorporating particular monomers or functional groups into a pre-existing polymer, the properties of the polymer can be modified. For example, co-polymerization of HEMA monomers with other monomers (such as methyl methacrylate) can be used to modify properties such as swelling and mechanical properties. Monomers may also be reacted with other compounds to form "macromonomers" (mentioned above) that are then included in the preferred polymers used in the present invention. For example, HEMA can be reacted with lactide to form a HEMA-polylactic acid polymer (HEMA-PLA), which itself can be used as a monomer in the polymers of the present invention. In addition, the monomers themselves may be combinations of monomer units, which are then incorporated into the polymer. An example of this type of monomer is oligo(ethyleneglycol) monomethyl ether methacrylate (OEGMA), which is a hydrophilic monomer composed of two hydrophilic monomers: ethylene glycol and methacrylate.

The preferred polymers used in the present invention may be further modified with one or more moieties and/or functional groups. Any moiety or functional group can be used as required. In some embodiments, polymers may be modified with polyethylene glycol (PEG), with a carbohydrate, and/or with acyclic polyacetals derived from polysaccharides. In addition, as discussed above, hydrophilic groups can be incorporated into monomers (and therefore polymers) to increase a polymer's water-binding capacity.

In terms of sequence, copolymers may be block copolymers, graft copolymers, random copolymers, blends, mixtures, and/or adducts of any of the foregoing and other polymers. Typically, polymers used in accordance with the present invention are organic polymers. Preferably, the polymers used in the present invention are biocompatible. In some embodiments, the polymers are biodegradable. In other embodiments, the polymers are both biocompatible and biodegradable.

The preferred polymers used in the present invention may also include other monomers in their structure. For example, the monomers may be polymers such as poly(vinyl alcohol) (PVA), polyesters, acrylic polymers and ionic polymers, or monomers of these.

If it is desired that the polymer be biodegradable or absorbable, one or more monomers having biodegradable linkages may be used. In the alternative, or in addition, the monomers may be chosen such that the product of the reaction between them results in a biodegradable linkage. For each approach, monomers and/or linkages may be chosen such that the resulting biodegradable polymer will degrade or be absorbed in a desired period of time. Preferably, the monomers and/or linkages are selected such that, when the polymer degrades under physiological conditions, the resulting products are nontoxic.

The biodegradable linkage may be chemically or enzymatically hydrolysable or absorbable. Illustrative chemically-hydrolysable biodegradable linkages include polymers, copolymers and oligomers of glycolide, lactide, caprolactone, dioxanone, and trimethylene carbonate. Illustrative enzymatically-hydrolysable biodegradable linkages include peptidic linkages cleavable by metalloproteinases and collagenases. Additional illustrative biodegradable linkages include polymers and copolymers of poly(hydroxyl acid)s, poly(orthocarbonate)s, poly(anhydride)s, poly(lactone)s, poly(aminoacid)s, poly(carbonate)s, and poly(phosphonate)s.

In one embodiment, the preferred polymer used in the present invention is a polymer of Formula (I):

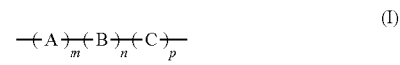

wherein A is a water-binding monomer, B is a monomer that is capable of imparting mechanical properties to a hydrogel, C is a monomer that has a functional group for binding to a NSPP, m is an integer from 1 to 20, n is an integer from 1 to 20, and p is an integer from 1 to 20.

The preferred polymer used in the present invention may accordingly be a polymer of Formula (Ia):

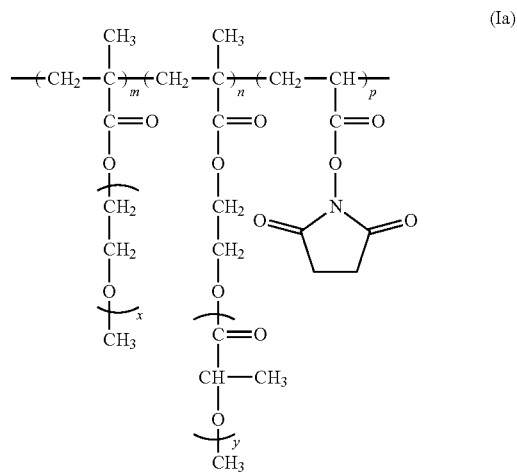

wherein A is the water-binding monomer OEGMA, B is the strengthening monomer HEMA-PLA, C is the crosslinker NAS, m, n and p are as defined above, x is an integer from 1 to 1000, and y is an integer from 1 to 1000.

When the preferred polymer used in the present invention includes a fourth monomer that is capable of imparting phase transition characteristics to the hydrogel, the polymer may be a polymer of the Formula (II):

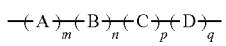
(II)

wherein A, B, C, m, n, and p are as defined above, D is a monomer that is capable of imparting phase transition characteristics to the hydrogel, and q is an integer from 1 to 10. An example of such a polymer is a polymer of Formula (IIa):

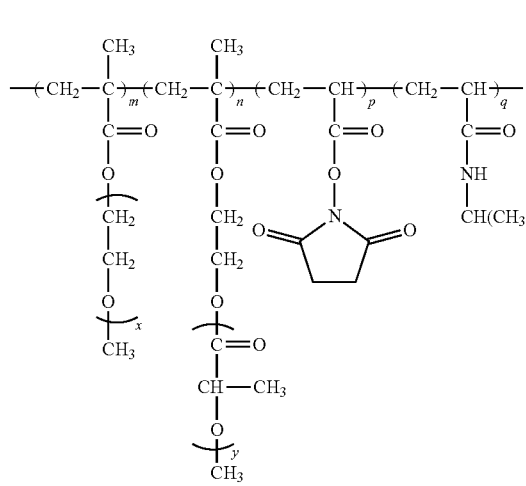

wherein A is the water-binding monomer OEGMA, B is the strengthening monomer HEMA-PLA, C is the crosslinker NAS, D is the phase-transition monomer NIPAAm, and m, n, p, q, x and y are as defined above.

It has also been discovered that some monomers, such as HEMA-PLA, polyesters such as poly(lactic acid), poly(caprolactone), poly(glycolide), and their random copolymers (e.g. poly(glycolide-co-lactide) and poly(glycolide-co-caprolactone) and other biodegradable and biocompatible polymers, can elevate the LCST of the preferred polymer used in the present invention during degradation of biodegradable segments (e.g. PLA) in vivo, leading to bioresorption of the polymer. This provides the additional advantage that the polymers used in the present invention may be designed so as to be biodegradable in vivo.

A person skilled in the art will be aware that the monomers A, B, C and D may be present in the polymer in any order, provided that the required water-binding, strengthening and/or cross-linking capabilities are achieved.

The overall size of the preferred polymer used in the present invention may differ, depending on factors such as the types of monomers that are incorporated into the polymer, the type of NSPP that is sought to be used to form the hydrogel, and the conditions under which the protein is to be coupled to the polymer. However, in general, the preferred polymer used in the present invention may be a molecule of about 1 to about 100 kDa, about 5 to about 60 kDa, or about 30 kDa.

A person skilled in the art will be aware of suitable methods of synthesising the preferred polymers used in the present invention. These include methods such as ring-opening polymerisation, addition polymerization (including free radical polymerization) and condensation polymerization.

A preferred polymer for use in bone regeneration is a polymer of Formula (IIa):

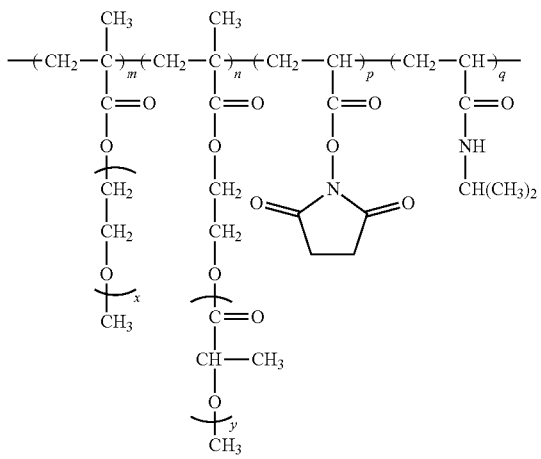

Based on Formula II:
A is oligo (ethylene) glycol monomethyl ether methacrylate OEGMA;
B is hydroxyethyl methacrylate poly(lactic acid) (HEMA-PLA);
C is N-acryloxysuccinimide (NAS); and
D is N-isopropylacrylamide (NIPAAm).

In addition, x is in the range of 1-1000 and y is in the range of 1-1000 and m, n, p, and q are in the range of 1-20. In one embodiment, preferably A is in an amount of about 2-8 mol %, B is in an amount of about 8-10 mol %, C is in an amount of about 14 mol % and D is in an amount of about 73 mol %. In other embodiments, A is included in an amount between 4 and 15 mol %, such as 5, 6, 7, 8, 9, 10, 11, 12, 13 or 14 mol %. B is preferably included in an amount between 4 and 15 mol %, such as 5, 6, 7, 8, 9, 10, 11, 12, 13 or 14 mol %. C is preferably included in an amount between 1 and 20 mol %, such as 2, 3, 4, 5, 6, 5 7, 8, 9, 10, 11, 12, 13, 14, 15, 16, 17, 18 or 19 mol %. D is preferably included in an amount which makes up the remainder to 100% of the polymer composition, for example, between about 60 and 90 mol %, such as 65, 70, 71, 72, 73, 74, 75, 76, 77, 78, 79, 80, 81, 82, 83, 84, 85, 86, 87, 88 or 89 mol %. The percentages recited herein relate to the composition of the final polymer and not the feed amounts utilised when forming the polymer.

In another embodiment: A is in an amount of about 2-8 mol % (for example about 2, 3, 4, 5, 6 or 7 mol %); B is in an amount of about 5-10 mol % (for example about 5, 6, 7, 8, 9 or 10 mol %), C is in an amount of about 14 mol % and D is in an amount of about 79 mol %.

B. Compositions for Forming Hydrogels

The present invention also relates to a preferred composition useful for forming a hydrogel for use in the invention, the composition including a NSPP and a polymer, the polymer comprising:
a first water-binding monomer; and
a second monomer that has a functional group that is bound to the NSPP,
wherein the binding of the NSPP to the second monomer crosslinks the polymer, thereby enabling formation of a hydrogel when the composition is contacted with water.

The term "composition", as used herein, refers to a solid or liquid composition containing the components mentioned above. In some embodiments, other components such as pharmaceutically-acceptable excipients and biologically active agents (e.g. drugs, vitamins and minerals), to assist in repair and/or re-generation of the target bone tissue, and/or to provide a method of achieving targeted delivery of biologically active compounds, may also be included in the preferred compositions used in the present invention.

In general, the amount of polymer in the composition used in the present invention is an amount that allows for the formation of hydrogels. In some embodiments, the amount of polymer in the composition ranges between: about 1% w/w and about 90% w/w, between about 2% w/w and about 80% w/w, between about 4% w/w and about 70% w/w, between about 5% w/w and about 60% w/w, between about 5% w/w and about 50% w/w, between about 6% w/w and about 40% w/w, between about 7% w/w and about 30% w/w or between about 8% w/w and about 20% w/w. In some embodiments, the amount of polymer is: about 1% w/w, about 2% w/w, about 3% w/w, about 4% w/w, about 5% w/w, about 6% w/w, about 7% w/w, about 8% w/w, about 9% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w or more. In some embodiments, the amount of polymer is approximately 85% w/w. As a general rule, the solidity of the hydrogel increases with higher polymer concentrations in the composition.

B1. Excipients and Biologically-Active Agents

Pharmaceutically-acceptable excipients may be included in the preferred compositions and/or hydrogels used in the present invention, and include any and all solvents, dispersion media, inert diluents, or other liquid vehicles, dispersion or suspension aids, granulating agents, surface active agents, disintegrating agents, isotonic agents, thickening or emulsifying agents, preservatives, binding agents, lubricants, buffering agents, oils, and the like, as suited to the particular dosage form desired. Remington (Gennaro, A. R., *Remington: The Science and Practice of Pharmacy*, 21st Ed (2006) Lippincott Williams & Wilkins) discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this invention.

Excipients such as colouring agents, coating agents, sweetening, flavouring, and perfuming agents can be present in the composition, according to the judgment of the formulator.

Biologically active agents or drug compounds that may be added to the preferred composition and/or hydrogel used in the present invention include proteins, glycosaminoglycans, carbohydrates, nucleic acids and inorganic and organic biologically active compounds, such as enzymes, antibiotics, anti-neoplastic agents, local anaesthetics, hormones, angiogenic agents, anti-angiogenic agents, growth factors (e.g. insulin-like growth factor-1 (IGF-1), basic fibroblast growth factor (bFGF) and transforming growth factor-b (TGFb)), antibodies, neurotransmitters, psychoactive drugs, anticancer drugs, chemotherapeutic drugs, drugs affecting reproductive organs, genes, and oligonucleotides.

A composition containing components such excipients and/or biologically active agents can be produced by combining a preferred polymer as disclosed herein with a NSPP, drying the resulting composition, and then combining this with one or more other components. The resulting composition may be in the form of a powder or other particulate form, to which water is then added to form a hydrogel, in accordance with the present invention. A hydrogel containing these components can therefore be produced simply by adding the desired aqueous solvent to the composition.

The amount of polymer, NSPP and biologically active agent present in the preferred composition to be used in the invention will necessarily depend upon the particular drug and the condition to be treated. A person skilled in the art will be aware of appropriate agents and amounts to use to treat the condition.

B2. Natural or Synthetic Peptide or Protein (NSPP)

In the context of the present invention, a NSPP is important because, as discussed above, it crosslinks polymers, which enables the polymers to form a hydrogel. The preferred hydrogels used in the present invention may be formed by, for example, exposing collagen to a polymer of Formula (I). The NSPP is also important because it provides additional mechanical properties (such as strength and resilience) to the hydrogel, as well as providing, at the repair site, an environment that mimics the natural environment, thereby assisting in bone tissue repair and re-generation.

In one embodiment the NSPP may be a combination of a range of different isoforms, for example, collagen type 1, 2, 3, 4, or a range of different proteins or peptides. Other synthetic peptides can be chosen from: Arg-Gly-Asp-Ser (RGDS), synthetic bone morphogen peptides, thymosin $\beta$-4, growth hormone segments, bone morphogenetic growth factors and insulin growth factors and splice variance of insulin growth factor such as mechano-growth factor.

It is important that the NSPP contains side chains or other functional groups that are exposed to enable reaction with the functional group of the NSPP-binding monomer(s), thereby binding the NSPP to the polymer through the NSPP-binding monomer(s). Examples of suitable side chains include glutamic acid or lysyl side chains.

The present invention also contemplates the use of variants of the NSPPs, for example species variants or polymorphic variants. The present invention is intended to cover all functionally active variants of the NSPPs that exhibit the same activity. This also includes apo- and haloforms of the NSPPs, post-translationally modified forms, as well as glycosylated or deglycosylated derivatives. Such functionally active fragments and variants include, for example, those having conservative amino acid substitutions.

In general, the amount of NSPP in the composition of the present invention is an amount that allows for the formation of hydrogels. In some embodiments, the amount of NSPP in the composition ranges between: about 0.01% w/w and about 60% w/w, between about 1% w/w and about 50% w/w, between about 1% w/w and about 40% w/w, between about 5% w/w and about 30% w/w, between about 5% w/w and about 20% w/w, or between about 5% w/w, or about 10% w/w. In some embodiments, the percent of NSPP is about 1% w/w, about 2% w/w, about 3% w/w, about 4% w/w, about 5% w/w, about 6% w/w, about 7% w/w, about 8% w/w, about 9% w/w, about 10% w/w, about 20% w/w, about 30% w/w, about 40% w/w, about 50% w/w, or more.

Preferably, the NSPP(s) for use in the present invention will be obtained from recombinant sources, although they can also be extracted from natural sources or synthesised.

C. Hydrogels

The present invention also relates to the use of a hydrogel including water, a NSPP and a polymer, the polymer including:

a first water-binding monomer; and a second monomer that is bindable to the NSPP, wherein the binding of the NSPP to the second monomer crosslinks the polymer, thereby forming a hydrogel, with the water contained therein.

In one embodiment, the hydrogel includes a polymer having a monomer described above for enabling phase transition of the hydrogel from liquid state at lower temperature to gel state at body temperature. One example of a monomer useful for this purpose is NIPAAm. It is a particularly surprising finding that an otherwise insoluble molecule, such as collagen, can be made to transition from liquid to gel state according to temperature profile by use of this monomer. Therefore, the advantage is that the preferred hydrogel used in the present invention, at cooler temperatures, can be administered easily by, for example, injection. The hydrogel is then transformed into a more viscous gel, which has the desired strength and elasticity properties, following warming in the body to the natural body temperature.

Having been provided with a polymer composition described above, the hydrogel may be formed by adding water to the composition in any way known to a person skilled in the art. Indeed, one advantage of the present invention is that the polymer does not need to be crosslinked in any way prior to contact with the NSPP, in order for a hydrogel to form.

C1. Cells

The preferred hydrogel for use in the present invention may also include cells to assist in repair and/or re-generation of the target bone tissue.

In general, cells to be used in accordance with the present invention are any types of cells. The cells should be viable when encapsulated within the preferred hydrogels used in the present invention. In some embodiments, cells that can be encapsulated within hydrogels include, but are not limited to: mammalian cells (e.g. human cells, primate cells, mammalian cells, rodent cells, etc.), avian cells, fish cells, insect cells, plant cells, fungal cells, bacterial cells, and hybrid cells. In some embodiments, exemplary cells that can be encapsulated within hydrogels include stem cells, totipotent cells, pluripotent cells, and/or embryonic stem cells. In some embodiments, exemplary cells that can be encapsulated within hydrogels include, but are not limited to, primary cells and/or cell lines from any tissue. For example: cardiomyocytes, myocytes, hepatocytes, keratinocytes, melanocytes, neurons, astrocytes, embryonic stem cells, adult stem cells, hematopoietic stem cells, hematopoietic cells (e.g. monocytes, neutrophils, macrophages, etc.), ameloblasts, fibroblasts, chondrocytes, osteoblasts, osteoclasts, neurons, sperm cells, egg cells, liver cells, epithelial cells from lung, epithelial cells from gut, epithelial cells from intestine, liver, epithelial cells from skin, etc., and/or hybrids thereof, may be encapsulated within preferred hydrogels used in accordance with the present invention.

Exemplary mammalian cells that can be encapsulated within the preferred hydrogels used in accordance with the present invention include, but are not limited to: Chinese hamster ovary (CHO) cells, Hela cells, Madin-Darby canine kidney (MOCK) cells, baby hamster kidney (BHK cells), NSO cells, MCF-7 cells, MDA-MB-438 cells, U87 cells, A172 cells, HL60 cells, A549 cells, SP10 cells, DOX cells, DG44 cells, HEK 293 cells, SHSY5Y, Jurkat cells, BCP-1 cells, COS cells, Vero cells, GH3 cells, 9L cells, 3T3 cells, MC3T3 cells, C3H-10T1/2 cells, NIH-3T3 cells, and C6/36 cells.

In some embodiments, it is desirable that cells are evenly distributed throughout a hydrogel. Even distribution can help provide more uniform tissue-like hydrogels that provide a more uniform environment for encapsulated cells. In some embodiments, cells are located on the surface of a hydrogel. In some embodiments, cells are located in the interior of a hydrogel. In some embodiments, cells are layered within a hydrogel. In some embodiments, the hydrogel contains different cell types.

In some embodiments, the conditions under which cells are encapsulated within hydrogels are altered in order to maximize cell viability. In some embodiments, for example, cell viability increases with lower polymer concentrations. In some embodiments, cells located at the periphery of a hydrogel tend to have decreased viability relative to cells that are fully-encapsulated within the hydrogel. In some embodiments, conditions (e.g. pH, ionic strength, nutrient availability, temperature, oxygen availability, osmolarity, etc.) of the surrounding environment may need to be regulated and/or altered to maximize cell viability.

In some embodiments, cell viability can be measured by monitoring one of many indicators of cell viability. In some embodiments, indicators of cell viability include, but are not limited to: intracellular esterase activity, plasma membrane integrity, metabolic activity, gene expression, and protein expression. To give but one example, when cells are exposed to a fluorogenic esterase substrate (e.g. calcein AM), live cells fluoresce green as a result of intracellular esterase activity that hydrolyses the esterase substrate to a green fluorescent product. To give another example, when cells are exposed to a fluorescent nucleic acid stain (e.g. ethidium homodimer-1), dead cells fluoresce red because their plasma membranes are compromised and, therefore, permeable to the high-affinity nucleic acid stain.

In general, the amount of cells in a composition is an amount that allows for the formation of preferred hydrogels for use in accordance with the present invention. In some embodiments, the amount of cells that is suitable for forming hydrogels ranges between: about 0.1% w/w and about 80% w/w, between about 1.0% w/w and about 50% w/w, between about 1.0% w/w and about 40% w/w, between about 1.0% w/w and about 30% w/w, between about 1.0% w/w and about 20% w/w, between about 1.0% w/w and about 10% w/w, between about 5.0% w/w and about 20% w/w, or between about 5.0% w/w and about 10% w/w. In some embodiments, the amount of cells in a composition that is suitable for forming hydrogels is approximately 5% w/w. In some embodiments, the concentration of cells in a precursor solution that is suitable for forming hydrogels ranges between about 10 and about $1\times10^8$ cells/mL, between about 100 and about $1\times10^7$ cells/mL, between about $1\times10^3$ and about $1\times10^6$ cells/mL, or between about $1\times10^4$ and about $1\times10^5$ cells/mL. In some embodiments, a single hydrogel comprises a population of identical cells and/or cell types. In some embodiments, a single hydrogel comprises a population of cells and/or cell types that are not identical. In some embodiments, a single hydrogel may comprise at least two different types of cells.

In some embodiments, a single hydrogel may comprise 3, 4, 5, 10, or more types of cells. To give but one example, in some embodiments, a single hydrogel may comprise only embryonic stem cells. In some embodiments, a single hydrogel may comprise both embryonic stem cells and hematopoietic stem cells.

C2. Media

Any of a variety of cell culture media, including complex media and/or serum-free culture media, that are capable of supporting growth of the one or more cell types or cell lines may be used to grow and/or maintain cells. Typically, a cell culture medium contains a buffer, salts, energy source, amino acids (e.g., natural amino acids, non-natural amino acids, etc.), vitamins, and/or trace elements. Cell culture media may optionally contain a variety of other ingredients, including but not limited to, carbon sources (e.g., natural sugars, non-natural sugars, etc.), cofactors, lipids, sugars, nucleosides, animal-derived components, hydrolysates, hormones, growth factors, surfactants, indicators, minerals, activators of specific enzymes, activators inhibitors of specific enzymes, enzymes, organics, and/or small molecule metabolites.

Cell culture media suitable for use in accordance with the present invention are commercially available from a variety of sources, e.g., ATCC (Manassas, Va.). In certain embodiments, one or more of the following media are used to grow cells: RPMI-1640 Medium, Dulbecco's Modified Eagle's Medium, Minimum Essential Medium Eagle, F-12K Medium, Iscove's Modified Dulbecco's Medium.

Those skilled in the art will recognize that the cells listed herein represent an exemplary, not comprehensive, list of cells that can be encapsulated within a precursor solution (and, therefore, eventually in a hydrogel) in accordance with the present invention.

D. Treatment of Bone

A therapeutically effective amount of a preferred hydrogel for use in the present invention may be delivered to a patient and/or organism prior to, simultaneously with, and/or after diagnosis with a disease, disorder, and/or condition. In some embodiments, a therapeutically-effective amount of a hydrogel is delivered to a patient and/or organism prior to, simultaneously with, and/or after onset of symptoms of a disease, disorder, and/or condition. Herein, the patient may be a human. Alternatively, the patient may be a non-human animal.

Accordingly, in one embodiment, disclosed herein is a method of repairing bone tissue, comprising administration of a therapeutically effective amount of a hydrogel as defined herein.

Also disclosed herein is the use of a therapeutically effective amount of a hydrogel as defined herein for repairing bone tissue.

Also disclosed herein is a hydrogel as defined herein for use in the repair of bone tissue, in any of the embodiments described in the specification.

Also disclosed herein is the use of a therapeutically effective amount of a hydrogel as defined herein for the manufacture of a medicament for repairing bone tissue.

Also disclosed herein is a hydrogel as defined herein when used in a method of repairing bone tissue.

In addition, disclosed herein is a composition having an active ingredient for use in repairing bone tissue, wherein the active ingredient is a hydrogel as defined herein.

Also disclosed herein is the use of a hydrogel as defined herein in repairing bone tissue, such as described above.

Furthermore, disclosed herein is the administration of the preferred hydrogel as defined herein to a desired site.

Herein, the term "therapeutically-effective amount", as used herein, refers to an amount of the preferred hydrogel for use in the present invention that is sufficient to treat, alleviate, ameliorate, relieve, delay onset of, inhibit progression of, reduce severity of, and/or reduce incidence of one or more symptoms or features of the disease, disorder, and/or condition. In particular, a "therapeutically-effective amount" is an amount sufficient to repair bone tissue. The term "repair" refers to the replacement or restoration of damaged bone tissue, preferably such that the original functionality of the damaged bone tissue is restored. A person skilled in the art will understand that the restoration may be complete, such that 100% of the original functionality has been restored, or may be partial, such that only a portion of the original functionality has been restored, or may be improved compared to the original tissue.

The preferred hydrogels for use in the present invention may be administered using any amount and any route of administration effective for treatment. The exact amount required will vary from subject to subject, depending on the species, age, and general condition of the subject, the severity of the infection, the particular hydrogel, its mode of administration, its mode of activity, and the like.

The preferred hydrogels for use in the present invention are typically formulated in dosage unit form for ease of administration and uniformity of dosage. It will be understood, however, that the total daily usage of the hydrogels and/or hydrogel assemblies will be decided by the attending physician within the scope of sound medical judgment.

The specific therapeutically effective dose level for any particular subject or organism will depend upon a variety of factors including the disorder being treated and the severity of the disorder; the activity of the specific active ingredient employed; the specific polymer and/or cells employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The preferred hydrogels for use in the present invention may be administered by any route. In some embodiments, the hydrogels are administered by a variety of routes, including direct administration to an affected site. For example, hydrogels may be administered locally near a site which is in need of bone tissue regeneration. Local administration may be achieved via injection of the cooled hydrogel directly to a site in need of bone tissue regrowth and/or repair.

In certain embodiments, the preferred hydrogels for use in the present invention may be administered such that encapsulated cells and/or therapeutic agents to be delivered are released at concentrations ranging from: about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered, for example, three times a day, two times a day, thrice a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

In some embodiments, the present invention encompasses "therapeutic cocktails" comprising the preferred hydrogels for use in the present invention. In some embodiments, hydrogels comprise a single cell type and, optionally, a therapeutic agent. In some embodiments, hydrogels comprise multiple different cell types and, optionally, a therapeutic agent.

It will be appreciated that cell-laden hydrogels can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, a hydrogel comprising a certain cell type to be used to promote bone tissue growth may be administered concurrently with another therapeutic agent used to stimulate growth of the same tissue), or they may achieve different effects (e.g., control of any adverse effects, such as inflammation, infection, etc.).

It has been discovered that, surprisingly, the polymers and hydrogels described herein are biocompatible with bone as indicated by their osteoconductive and osteoinductive properties. The polymer is particularly suited for the regeneration of bone. In one embodiment, the polymer is useful in the development of 3D scaffolds which promote migration, proliferation and differentiation of bone and endothelial cells, for example in orthopaedic and maxillofacial surgeries, and yet provides sufficient mechanical properties for load-bearing parts. The polymer supports bone tissue regeneration/formation and vascularisation and yet also provides minimal fibrotic reactions. In one form, the present invention provides scaffolds for osteochondral defects. The material of the invention is also useful as a coating for skeletal tissue regeneration. The present invention also finds use in cosmetic purposes over and above reconstruction and repair purposes. The present invention finds particular relevance for maxillofacial reconstruction applications, and dental applications.

Preferably, the material of the invention is biocompatible when placed in physiological fluid. Preferably, the biocompatible material of the invention forms a hydroxyapatite layer upon exposure to bodily fluids. As the skilled person will appreciate, the formation of hydroxyapatite is widely recognised as strong evidence that the body accepts the material as sui generis and is a requirement for the implant to chemically bond with living bone.

The polymer described herein are particularly useful as medical devices chosen from the group consisting of: a 3D implantable scaffold, an orthopaedic implant for reconstructive surgery, a dental implant/prostheses, a spine implant, implants for craniofacial reconstruction and alveolar ridge augmentation, an osteochondral defect implant, scaffolds for osteochondral defect, scaffolds for bone tissue regeneration and maxillofacial reconstruction that promote vascularisation and bone tissue ingrowth. However, it will be appreciated that there are many other devices which would be within the scope of the present invention.

The preferred polymers of the invention have many properties that make them suitable for use as implants, including relatively high mechanical strength, high structural stability, fatigue resistance, corrosion resistance, and biocompatibility. The implants may be implanted in: animals, non-limiting examples of which include reptiles, birds, and mammals, with humans being particularly preferred. Preferably, the compressive strength of the polymers is between about 2 to 15 MPa.

According to another aspect there is provided use of the polymers disclosed herein for forming osseous tissue on an orthopaedic defect upon contacting said defect with said polymer for a predetermined period, or by contacting a relevant area of a patient in need of treatment with an effective regenerating amount of said polymer. The uses of the present invention are manifold. In one or more embodiments it may be useful for: bone void fillings or augmentation in zones requiring cancellous rather than cortical bone; filling of bone defects after trauma, reconstruction, or correction in non-load or load-bearing indications; trauma and orthopaedics; filling of voids caused by cysts or osteotomies, filling of defects arising from impacted fractures, refilling of cancellous bone-harvesting sites, arthrodesis and non-unions; spine surgery: postero-lateral fusion, interbody fusion (as cage-filling material), vertebrectomies (as filling material of the vertebral implants), refilling of bone graft-harvesting sites, or cranio-maxillofacial surgery.

E. Kits

Disclosed herein are a variety of kits comprising one or more of the preferred hydrogels for use in the present invention. For example, the invention provides a kit comprising a hydrogel and instructions for use in repairing or regenerating bone defects. A kit may comprise multiple different hydrogels. A kit may optionally comprise polymers, cells, NSPP(s), biologically-active compounds, water, and the like. A kit may comprise any of a number of additional components or reagents in any combination. All of the various combinations are not set forth explicitly but each combination is included in the scope of the invention. A few exemplary kits that are provided in accordance with the present invention are described in the following paragraphs.

According to certain embodiments of the invention, a kit may include, for example, (i) a solution comprising a polymer, a solution comprising NSPP; and (ii) instructions for forming a hydrogel from the solution.

According to another embodiment, a kit may include, for example:
 (i) a composition comprising a polymer and NSPP; and
 (ii) instructions for forming a hydrogel from the composition.

According to another embodiment, a kit may include, for example, (i) a composition comprising a polymer and NSPP, one or both being in solid form; optionally a solvent such as water or the like, and (ii) instructions for forming a hydrogel from the composition.

Kits may further include other materials desirable from a commercial and user standpoint, including other buffers, diluents, filters, needles, and syringes.

Kits typically include instructions for use of the preferred hydrogels for use in the present invention. Instructions may, for example, comprise protocols and/or describe conditions for production of hydrogels, administration of hydrogels to a subject in need thereof, production of hydrogel assemblies, etc. Kits will generally include one or more vessels or containers so that some or all of the individual components and reagents may be separately housed. Kits may also include a means for enclosing individual containers in relatively close confinement for commercial sale, e.g., a plastic box, in which instructions, packaging materials such as styrofoam, etc., may be enclosed.

The kit or "article of manufacture" may comprise a container and a label or package insert on or associated with the container. Suitable containers include, for example, bottles, vials, syringes, blister packs, etc. The containers may be formed from a variety of materials such as glass or plastic. The container holds the hydrogel or composition which is effective for treating the condition and may have a sterile access port (for example the container may be an intravenous solution bag or a vial having a stopper pierceable by a hypodermic injection needle). The label or package insert indicates that the hydrogel or composition is used for treating the condition of choice. In one embodiment, the label or package insert includes instructions for use and indicates that the therapeutic composition can be used to repair or regenerate tissue.

EXAMPLE EMBODIMENTS

The preferred polymer used in the invention is PNPHO, which is conjugated with protein or peptide (NSPP), where both the protein/peptide segment and PNPHO have defined roles. The protein/peptide:

(a) serves as the source of bioactive signalling for bone regeneration; and (b) promotes the formation of blood vessels within and around the hydrogel filler.

The PNPHO polymer is chemically bonded with protein/peptide to:

(a) adjust the physicochemical properties of this biopolymer for bone applications;

(b) to impart rapid thermosetting to the hydrogel filler to confine it locally; and (c) to impart bioresorption properties to the injectable hydrogels.

The combination of these two main segments results in the formation of the new class of smart bone fillers with a range of favourable properties for bone healing. An advantage of the PNPHO polymer is that all its components are approved by the FDA for use in biomedical applications.

The PNPHO polymer comprises a thermally responsive fraction (N-isopropyl acrylamide) to induce the hydrogel formation at body temperature, along with lactide, ethylene glycol and N-acryloxysuccinimide segments to impart respectively, a high mechanical strength, water solubility, and amine group reactivity to the product. The molecular structure of the PNPHO polymer and the role of each segment are schematically shown in the schemes drawn below.

EXAMPLES

Materials

Chemicals were purchased from Sigma-Aldrich unless otherwise stated.

Stannous 2-ethylhexanoate ($Sn(Oct)_2$), N-isopropylacrylamide (NIPAAm), 2-hydroxyethyl methacrylate (HEMA), 4,4'-azobis(4-cyanovaleric acid) (ACVA) and N-acryloxysuccinimide (NAS) were used as received. Oligo(ethylene glycol) monomethyl ether methacrylate (OEGMA, $M_n$=475) was purified by passing its solution in dichloromethane (with 1:1 volume ratio) through a neutral alumina column to remove the inhibitor prior to use. D, L-lactide (LA) monomer was dried under vacuum at 40° C. for 24 hours prior to use. Azobisisobutyronitrile (AIBN) was kindly gifted by School of Chemistry in University of Sydney.

Synthesis of HEMA-Poly(Lactide) (HEMA-PLA) Macromonomer

HEMA-PLA macromonomer was synthesized by ring-opening polymerization of LA with the hydroxyl group of HEMA as the initiator and $Sn(Oct)_2$ as the catalyst (Scheme 1).

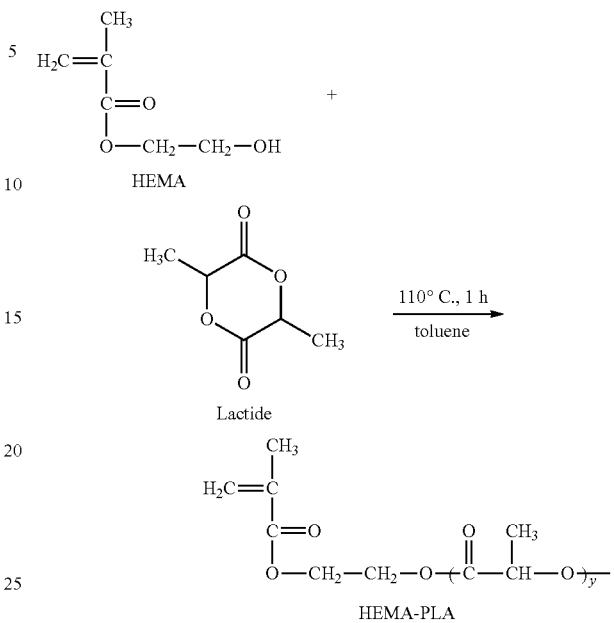

Scheme 1. Synthesis of HEMA-PLA macromonomer

LA and HEMA were mixed in a three-neck flask at 110° C. under a nitrogen atmosphere for 15 minutes. Subsequently, a mixture of 1 mol % of $Sn(Oct)_2$ (with respect to the HEMA feed) in 1 ml of anhydrous toluene was added to the LA/HEMA solution. The resulting mixture was stirred at 300 rpm and 110° C. for 1 hour under a nitrogen atmosphere. After the reaction, the mixture was dissolved in tetrahydrofuran and precipitated in cold distilled water at 1° C. The formed precipitate was separated by centrifugation at 3000 rpm for 5 minutes. The centrifugation cycle was repeated three times to remove all unreacted monomers and by-products (mainly salts). The precipitate was then dissolved in ethyl acetate. The suspended solid particles were removed from the solution with centrifugation at 6000 rpm for 5 minutes and the supernatant was dried with $MgSO_4$ for 12 hours. The dried supernatant was filtered to remove the $MgSO_4$ particles. The polymeric solution was then dried at 60° C. under reduced pressure and the residue of solvent was further removed under vacuum, at 40° C. for 24 hours. The resultant viscous oil was stored in a fridge for further use.

The feed ratio of HEMA:LA was varied from 1:1.5 and 1:2.5 to obtain PLA/HEMA macromonomers with different lactate lengths. Two PLA/HEMA macromonomers with lactate lengths of 3 and 6 were synthesized by using 1:1.5 and 1:2.5 mol ratio of HEMA to LA monomers, respectively.

The synthesis of PLA/HEMA macromonomer was confirmed, using $^1H$ NMR spectra with evidence of proton peaks from both HEMA and LA. The molar ratio of LA to HEMA in the PLA/HEMA macromonomer was calculated from $^1H$ NMR spectra using the peaks at 5.2 ppm for methine in lactate, and total integrations at 5.7 ppm and 6.0 ppm peaks for HEMA.

Synthesis of Poly(NIPAAm-Co-NAS-Co-(HEMA-PLA)-Co-OEGMA) (PNPHO)

PNPHO was synthesised using either method (1) or (2) as described below (Scheme 2).

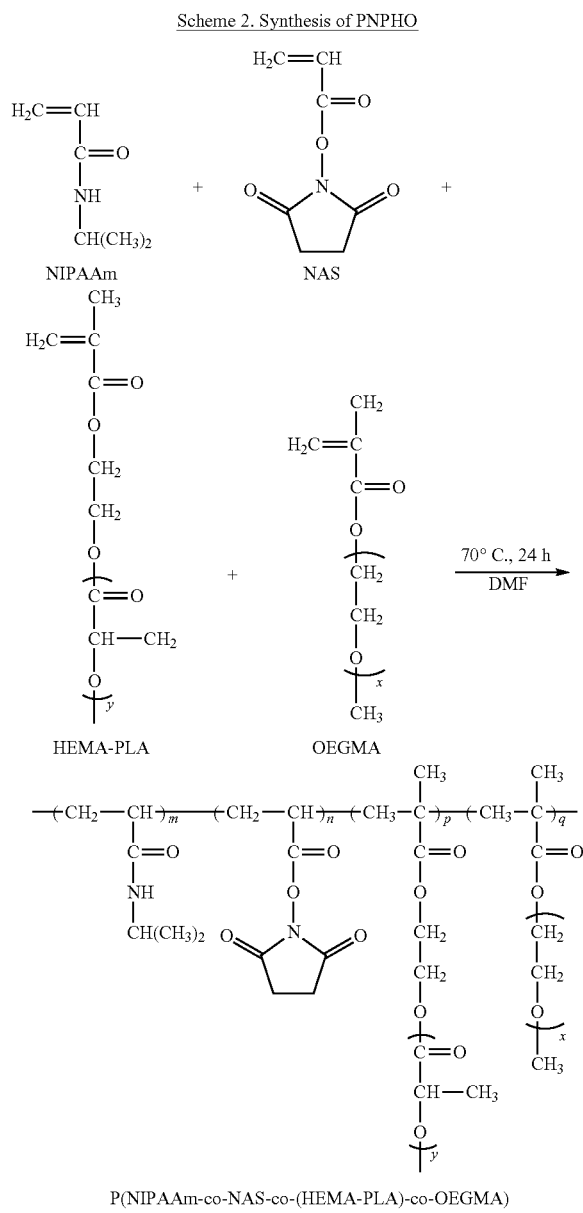

Scheme 2. Synthesis of PNPHO

P(NIPAAm-co-NAS-co-(HEMA-PLA)-co-OEGMA)

Method 1

PNPHO was synthesized by free radical polymerization using AIBN as the initiator. A Schlenk flask with a magnetic stir bar and a rubber septum was charged with NIPAAm (12 mmol), NAS (1.0 mmol), HEMA-PLA (0.57 mmol), OEGMA (0.56 mmol), AIBN (0.07 mmol) and anhydrous N,N'-dimethylformamide (DMF). The flask was deoxygenated by three freeze-pump-thaw cycles, and then sealed followed by immersing the flask into an oil bath preheated at 70° C. to start the polymerisation. After 24 hours, the reaction mixture was cooled to room temperature, precipitated in diethyl ether, filtered, and then dried under vacuum. The polymer was purified twice by redissolving/reprecipitating with THF/ethyl ether and finally dried under vacuum for 2 days.

Method 2

PNPHO was synthesized by free radical polymerization, using ACVA as the initiator. The composition of the copolymer was changed by varying the lactate length (3 and 6 in HEMA-PLA) and the molar ratios of HEMA-PLA (6, 8, and 11 mol %) and OEGMA (3, 5, and 8 mol %). Known amounts of NIPAAm, NAS, HEMA-PLA, OEGMA, ACVA ($7.0 \times 10^{-5}$ mol) were dissolved in 13 ml anhydrous N,N'-dimethylformamide in a round bottom, one neck flask. The system was then deoxygenated by 15 minutes of nitrogen purging. The results also showed that it is feasible to deoxygenate the monomer solution by purging nitrogen gas for 10 minutes in the solution under vacuum. This technique provides a more efficient method to remove oxygen from solution in large scales. The reactor was then sealed and immersed in an oil bath at 70° C. for 24 hours. The resultant polymeric solution was then cooled at room temperature for 1 hour and precipitated in 250 ml diethyl ether. The precipitate was then collected by filtering the suspension and dried under vacuum for 6 hours. The dried powder was dissolved in tetrahydrofuran and precipitated in diethyl ether to further remove residues of macromonomers. The final powder was dried under vacuum for at least 48 hours.

PNPHO Compositions

Figure 2A:
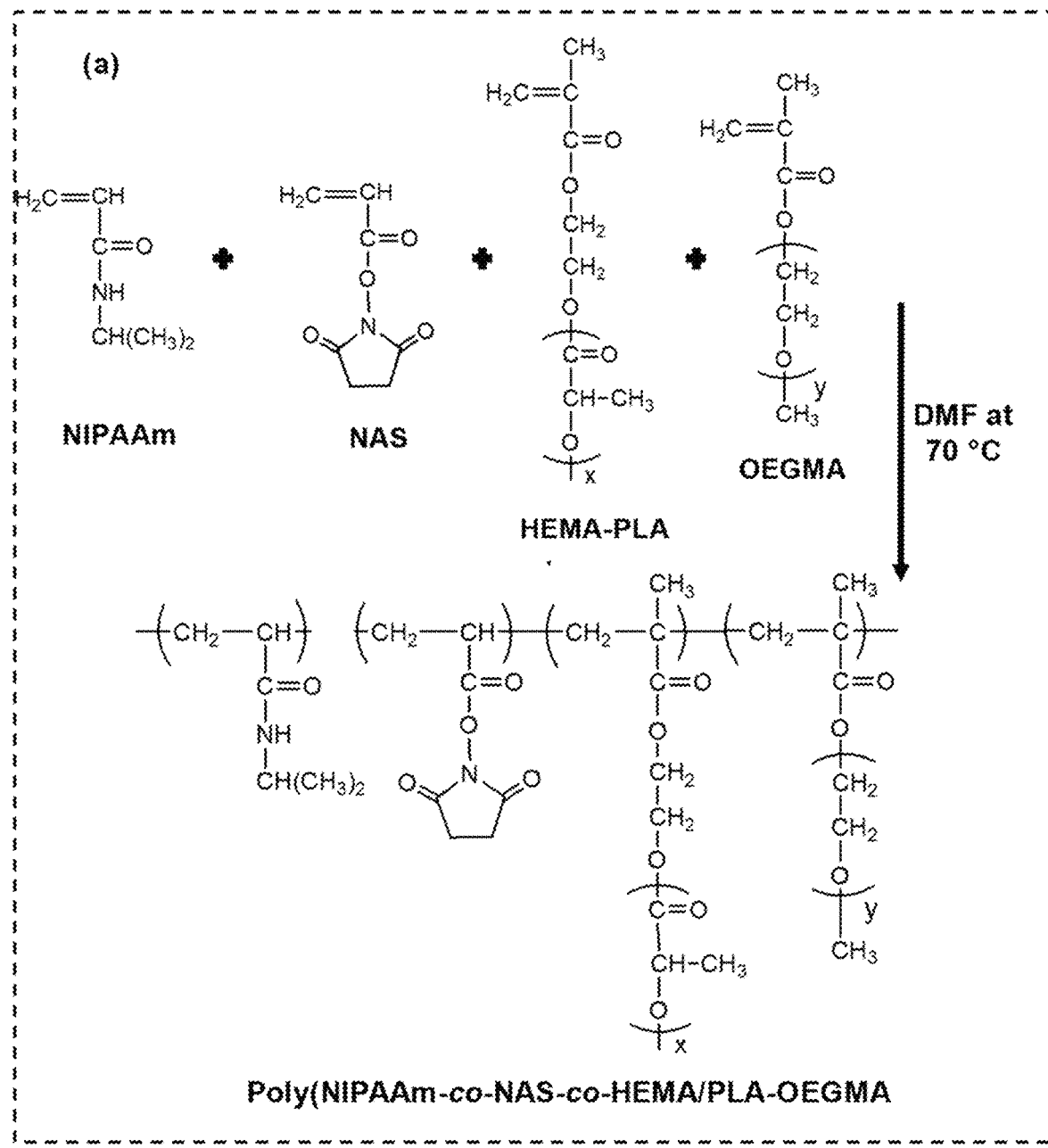
FIG. 2a: Synthetic preparation of PNPHO
Figure 2B:
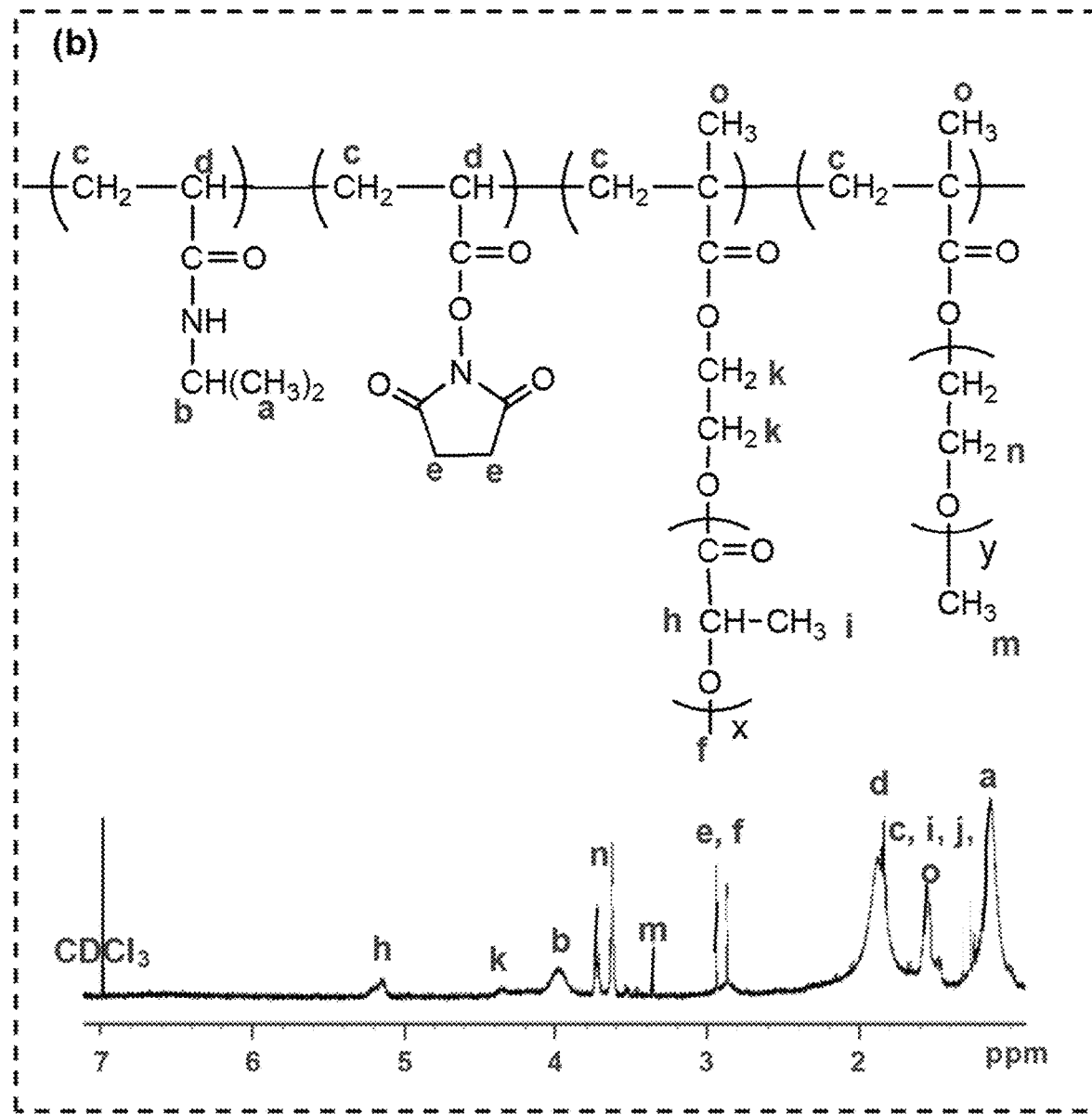
FIG. 2b: $^1$H NMR spectrum of PNPHO.

The synthesis of PNPHO copolymers was confirmed with $^1$H NMR spectra with evidence of proton peaks for each monomer, as shown in FIG. 2b. Characteristic proton peaks were detected for NIPAAm (a and b), NAS (e), HEMA-PLA (f, h, k), and OEGMA (m and n). The final composition of copolymer was calculated based on the integration of these peaks from each monomer as for NIPAAm (a), NAS(e/2-f), HEMA-PLA (h), and OEGMA (n/2). In this study copolymer is denoted as PNPHO and the subscript is added that corresponds to HEMA-PLA (lactate length) to OEGMA molar ratios. For example $PNPHO_{8(6)3}$ stands for the copolymer synthesized with 8 mol % HEMA-PLA with lactate length of 6, and 3 mol % OEGMA. Various copolymers were produced. These are shown in Table 1. Table 1 also provides data on their gelation time and temperature.

TABLE 1

PNPHO polymers according to the invention (in the form PLA/HEMA(LA length)/OEGMA/NAS/NIPAAm)

| Monomer Feed | Final Composition | Gelation Time (min) | Gelation Temp (° C.) |
|---|---|---|---|
| 8(5)/5/3.5/83 | 7.9(5)/4.8/7/80 | 2.5 ± 0.6 | 26.4 ± 1.9 |
| 8(5)/5/7/80 | 7.8(5)/4.6/13.6/74 | 3.1 ± 0.9 | 25.4 ± 2.6 |
| 6(5)/8/3.5/82 | 5.4(5)/8/7/80 | 5.1 ± 0.6 | 30.1 ± 1.6 |
| 6(5)/8/7/80 | 5.1(5)/8/14/72 | 5.4 ± 0.1 | 29.4 ± 3.1 |
| 8(5)/3/3.5/72 | 7.9(5)/4.8/7/80 | 2.0 ± 0.2 | 22.1 ± 2.1 |
| 8(5)/3/7/80 | 7.8(5)/4.6/13.6/74 | 2.2 ± 0.9 | 21.4 ± 3.0 |

Solubility of PNPHO in PBS

The monomer ratios of PNPHO were modified to acquire a range of compositions that were dissolved in aqueous media, such as PBS for the development of injectable formulations. NIPAAm-based copolymers are soluble in aqueous solutions below their LCST due to the formation of hydrogen bonds between the copolymer polar groups and water molecules. In this study the effects of lactate length, HEMA-PLA and OEGMA contents on the solubility of PNPHO were studied by measuring the saturation concentration of different compositions of PNPHO in PBS.

Figure 3:
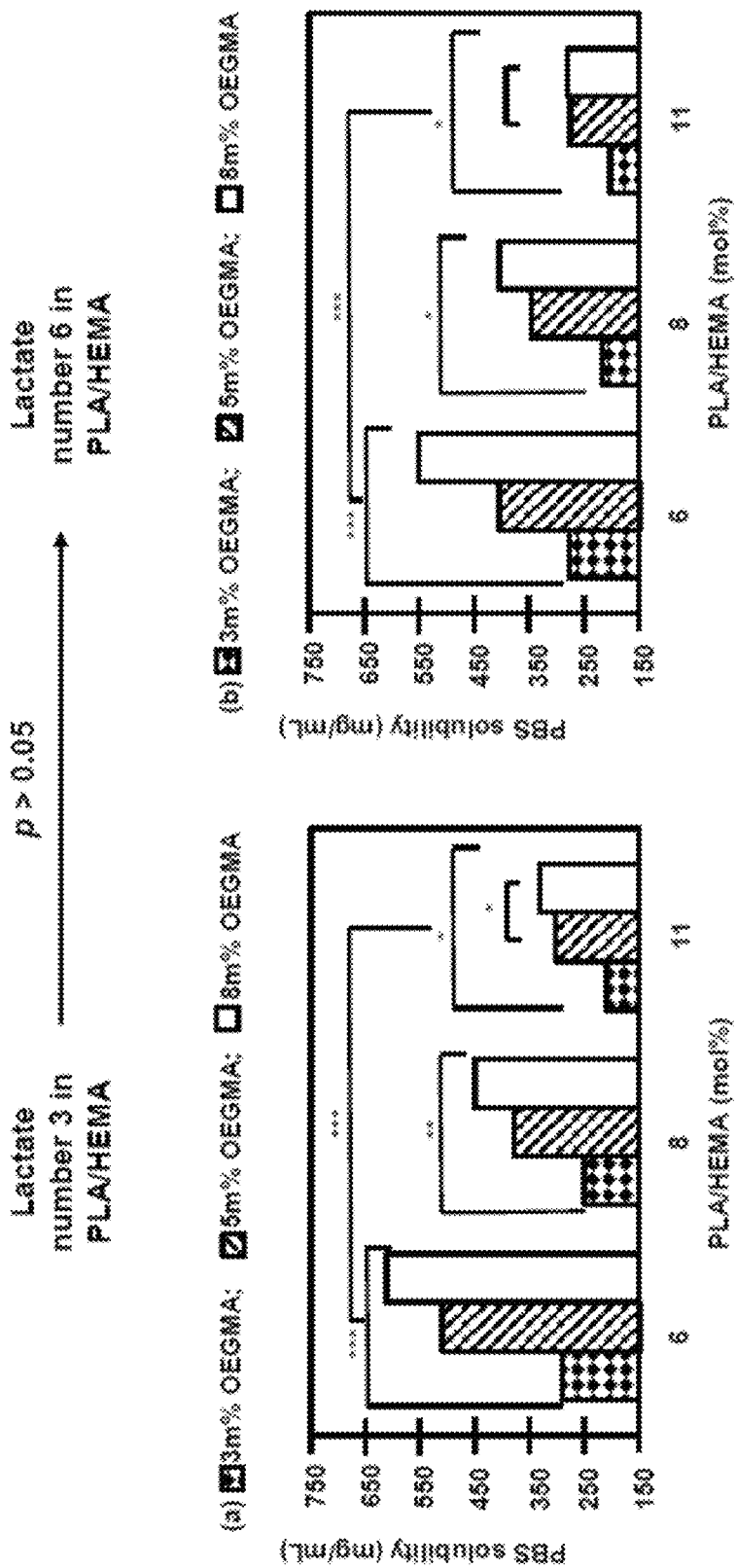
FIG. 3: Solubility of copolymers synthesized at different mole fraction of HEMA-PLA in aqueous solution at 4° C. for lactate number of 3 (a) and 6 (b), (*, , and * represent p<0.05, <0.01, and <0.001, respectively).

The results in FIG. 3 demonstrate that increasing lactate length within the range of 3 to 6 in the HEMA-PLA backbone had no significant impact on the solubility of PNPHO in PBS (p>0.05). Hydrophobic properties of a side chain in the backbone of PNPHO therefore had minimal impact on overall solubility of PNPHO in aqueous media, within the range examined. Therefore, by changing the lactate length, other characteristics of PNPHO, such as gelling behaviour and mechanical properties, can be tuned without affecting the solubility of PNPHO in an aqueous media.

The solubility of PNPHO in PBS can be tuned by changing both hydrophobic and hydrophilic contents. The PLA segment is the main hydrophobic backbone, while both NAS and HEMA monomers exhibit relatively limited hydrophilic properties. OEGMA was therefore included in the synthesis of PNPHO to promote the hydrophilic properties of the copolymer. Increasing HEMA-PLA (i.e. the hydrophobic content) in copolymers from 6 to 8 and 11 mol % decreased the solubility of PNPHO in PBS by 30% and 50%, respectively. For example, saturation concentration of $PNPHO_{6(6)3}$ was significantly ($p<0.001$) decreased from $250\pm17$ mg/ml to $190\pm10$ mg/ml and $164\pm6$ mg/ml in $PNPHO_{8(6)3}$ and $PNPHO_{11(6)3}$, respectively. This solubility reduction was also due to decreasing the concentration of the relatively hydrophilic segment NIPAAm in the copolymer ($p<0.05$). Therefore, decreasing NIPAAm content in PNPHO substantially affected the hydration of the copolymer.

The solubility of PNPHO in water was increased dramatically, when using more than 3 mol % (e.g. 1.5 mol %) OEGMA as a hydrophilic segment. Results showed that copolymers with OEGMA contents of less than 3 mol % were not soluble in aqueous media. The results in FIG. 3 show that the solubility of PNPHO copolymers with 6 mol % PLA-HEMA was significantly increased 2- and 3-fold when elevating the OEGMA concentration from 3 mol % to 5 and 8 mol %, respectively. However, in copolymers that contained a higher molar ratio of hydrophobic segment HEMA-PLA (i.e. 8 mol % and 11 mol %), OEGMA concentration had little effect on the solubility of PNPHO. This behaviour was attributed to formation of copolymers with longer chains and higher Mw, which impeded the hydration and solubility of the copolymer in aqueous solution. As an illustration, the molecular weight of $PNPHO_{11(3)8}$ was significantly ($p<0.01$) higher than $PNPHO_{11(3)5}$ (27K compared to 26K), which compromised the effect of its higher hydrophilic content, and therefore the saturation concentration for both compounds was approximately 300 mg/ml.

The effect of concentration of water soluble PNPHO copolymers on the injectability of their solutions through an 18 G needle was assessed. It was found that 150 mg/ml PNPHO solution in PBS was injectable through 18 G needle and this concentration of copolymer was used for further analysis. Higher concentrations of polymers can be used for other biomedical applications such as scaffold fabrication for in vitro tissue growth.

Conjugation of PNPHO with Naturally Derived Proteins and Formation of Hydrogels

The presence of the succinimide ester group in the molecular structure of PNPHO provided facial active sites for conjugation with NSPP such as collagen. Different conjugation techniques (as shown in FIG. 1) were used to prepare NSPP-copolymer hydrogels.

Collagen

Figure 4:
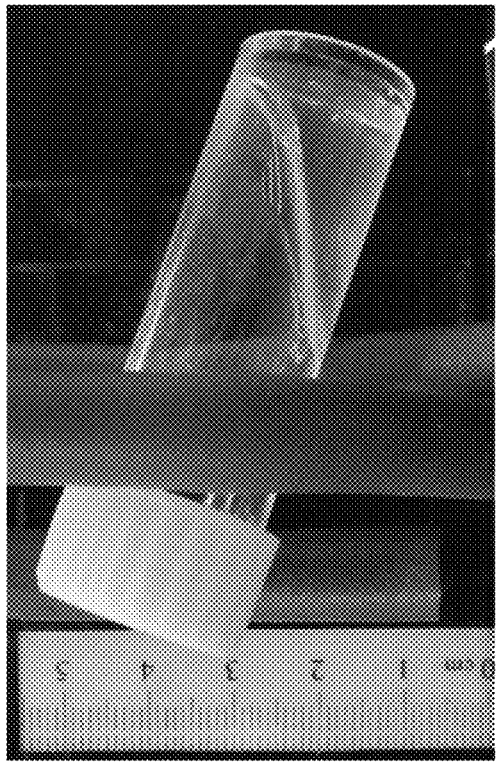
FIG. 4: Macroscopic image of the hydrogel (polymer and NSPP) formed at 37° C.
Figure 4:
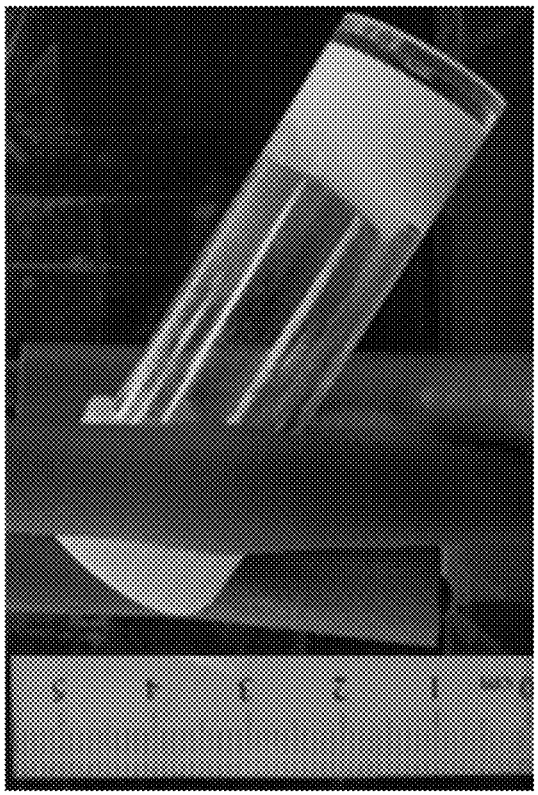

Since the succinimide linker exhibits high reactivity and optimized accessibility towards compounds containing amino groups, it is reasonable to postulate that the polymer can be applied to other types of natural polymers with amino groups for the fabrication of injectable hydrogels. To confirm this assumption the feasibility of a reaction between the polymer and collagen was examined. A collagen solution (OVICOLL® CLEAR, 1%, pH 2.5-3.5) was neutralized with small aliquots of 1 M NaOH solution. 250 micro litres of the resulting neutralized collagen solution was thoroughly mixed with 500 micro litres of 250 mg/l ml polymer/PBS solution. The mixture was then transferred to a refrigerator. After preservation at 4° C. for 24 hours, the mixture was then allowed to gel at 37° C. followed by washing with distilled water to remove any impurities. The results (FIG. 4) show the successful formation of hydrogel.

Gelling Behaviour (Time and Temperature)

The results in Table 1 showed that the gelling time of the hydrogels fabricated with PNPHO composition of 8(6)/5/3.5/83, 8(6)/5/7/80, 6(6)/8/3.5/82, and 6(6)/8/7/80 were within the range of 2.5 to 5 minutes. This gelation time is favourable for clinical applications as fast gelation may block the delivery needle and premature solidification of the formulation prior to delivery. In addition, the gelation temperatures of these formulations of PNPHO are above room temperature. The high gelation temperatures of the formulations are of great convenient for clinicians to deliver the solutions in vivo.

Conjugation Efficiency of PNPHO

Figure 5:
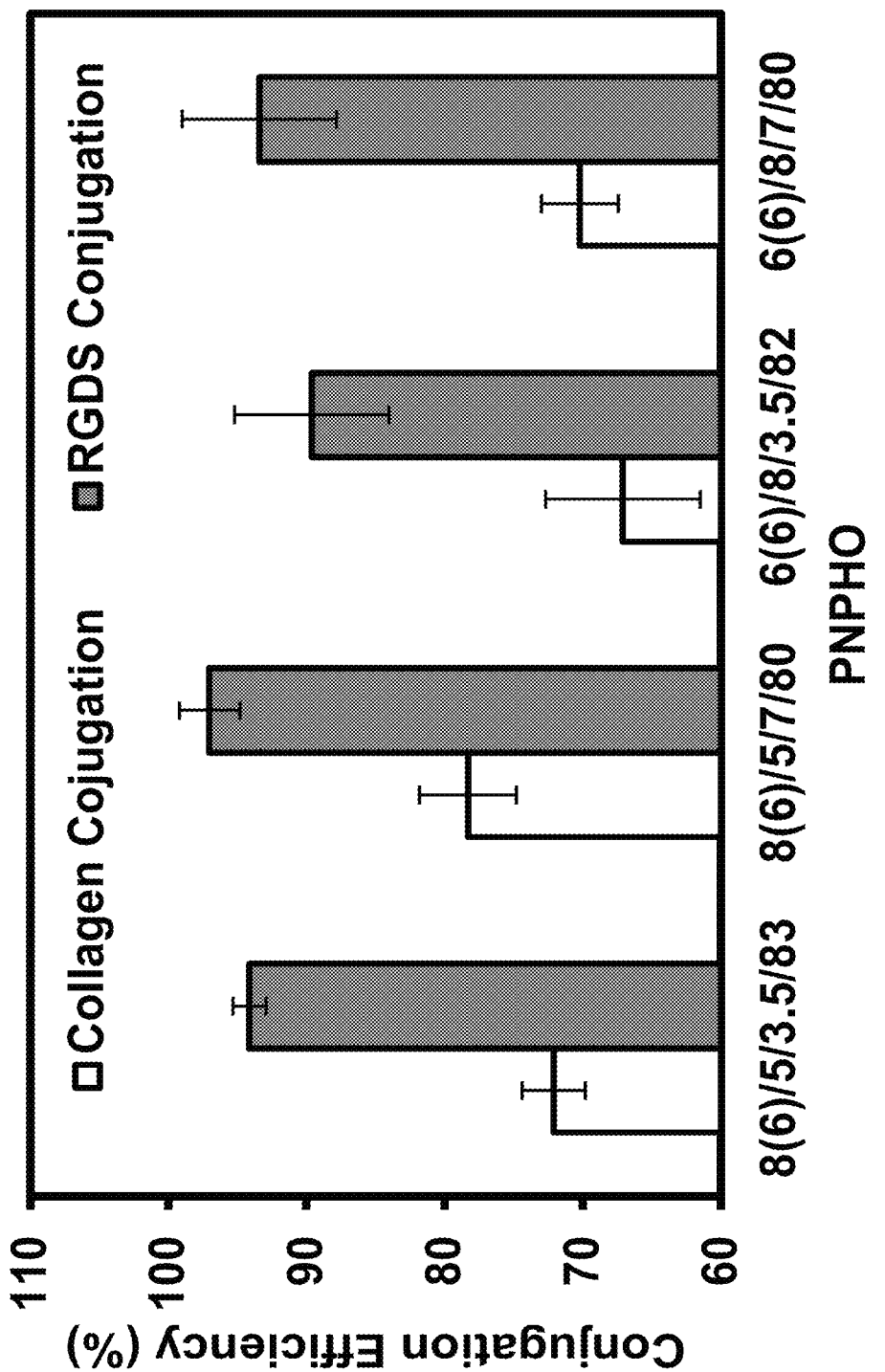
FIG. 5: ALP reading of the osteoblast cells culture on PNPHO-NSPP hydrogels.

The conjugation efficiency of the different formulations of PNPHO in Table 1 is shown in FIG. 5. For this analysis, 3 mol % collagen and Gly-Arg-Gly-Asp-Ser (GRGDS) synthetic peptide were used as model natural protein and synthetic peptides, respectively. The results indicated that nearly 70% of added collagen was conjugated with different PNPHO formulations. This result showed the high efficiency of the PNPHO to conjugate and deliver large natural molecules such as collagen. The conjugation efficiency of PNPHO with synthetic peptide was outstanding. Nearly 95% of small synthetic peptides could be conjugated with PNPHO.

Bioresorbable Behaviour of Protein-PNPHO Hydrogels

Figure 6:
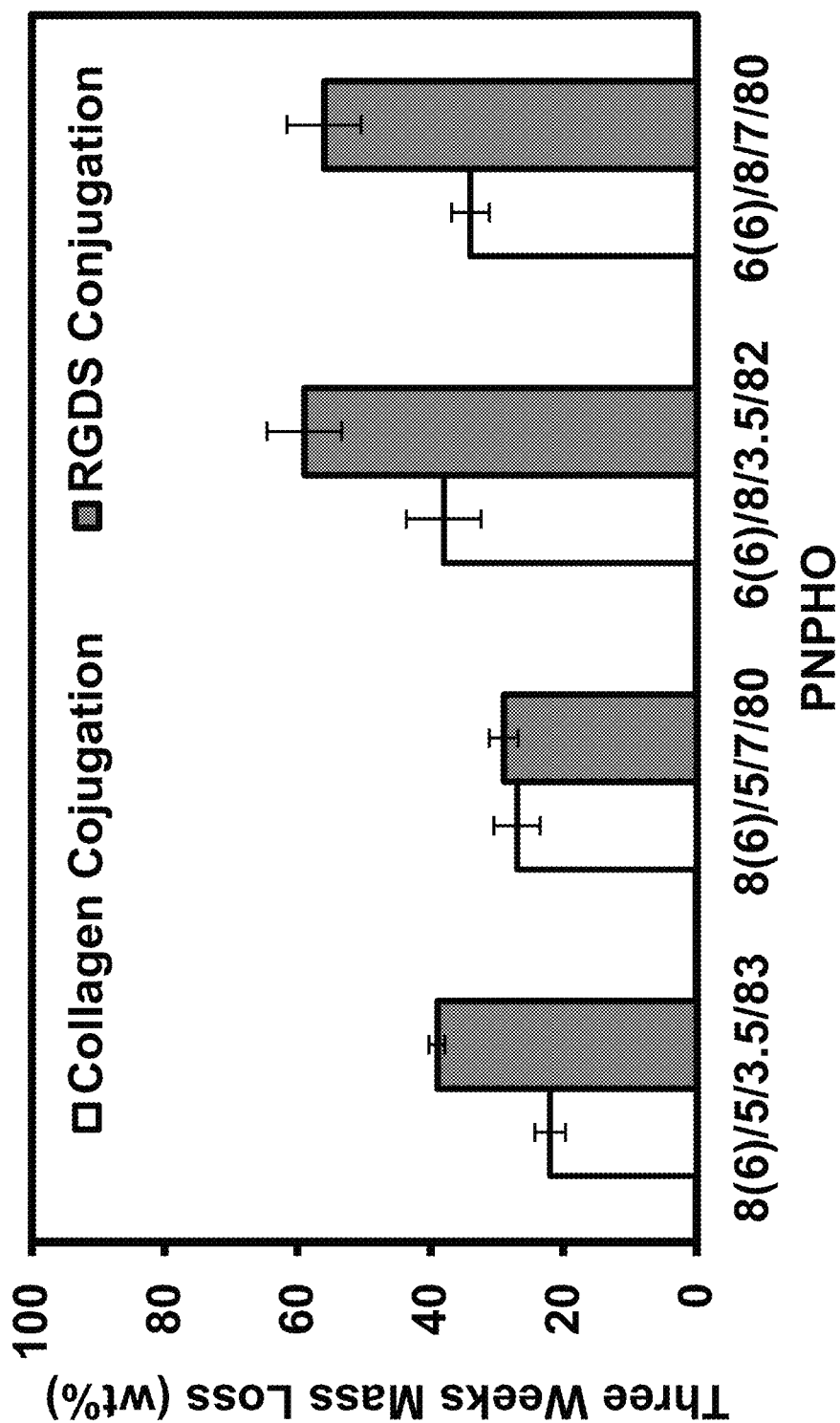
FIG. 6: Bioresorption behaviour of different formulations of PNPHO, conjugated with collagen.

The bioresorption behaviour of different formulations of PNPHO, conjugated with different NSPPs was studied by soaking hydrogels in phosphate buffered saline (PBS) at 37° C. to simulate physiological conditions. The results in FIG. 6 showed that 3 weeks post-incubation different formulations of PNPHO-NSPPs displayed significant mass loss, e.g. 20%-60%). These results confirmed the Bioresorbability of the PNPHO-NSPP hydrogels fabricated with different formulations of PNPHO and natural and synthetic proteins/peptides.

Biological Studies

Osteoblasts

Figure 7:
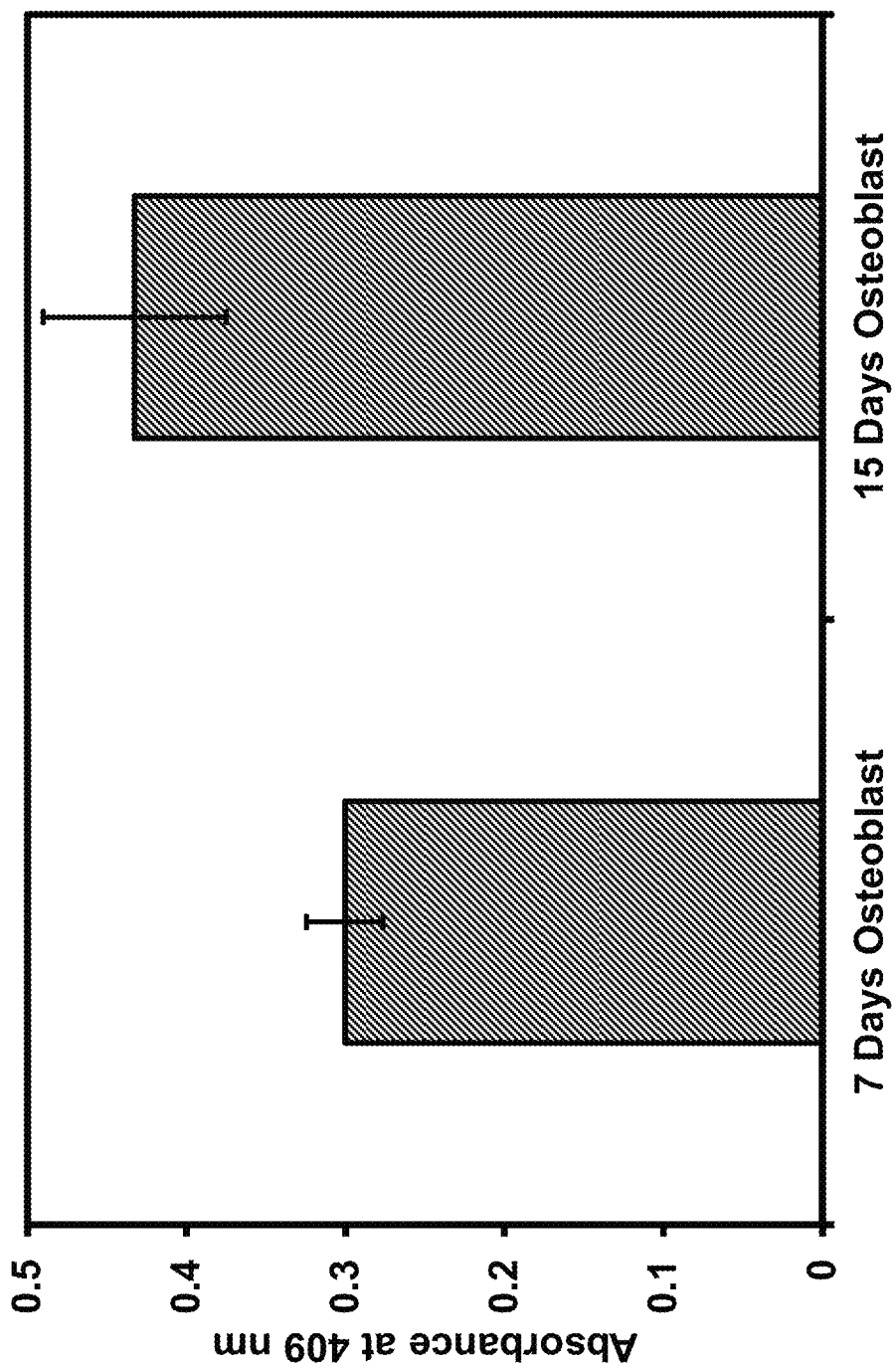
FIG. 7: Collagen-PNPHO cytocompatibility data.

SaSo2 cells were used to confirm the cytocompatibility of different PNPHO based hydrogels. Collagen-PNPHO was used as a model system. The result in FIG. 7 showed that the number of cells within the hydrogels was significantly increased from 7 days to 15 days post-culture. This result confirmed the cytocompatibility of the fabricated PNPHO based hydrogels.

Fabrication and Characterisation of the Peptide-PNPHO Hydrogels

A PNPHO-peptide precursor solution was found to be injectable through a very fine 29 G gauge needle with minimal thumb backpressure for the surgeon. Upon the increase of temperature to 37° C., the hydrogel solution formed an elastic robust hydrogel in 2 minutes. The fast gelation time and tissue adhesive properties of this hydrogel filler minimised the risk of dislocation or leakage of the hydrogel to the surrounding tissues. The thermosetting reaction of this hydrogel system is biologically benign. This has been confirmed via an in vitro study which showed that >95% of encapsulated cells are consistently viable after hydrogel formation. The mechanical strength of the hydrogel reaches its maximum value within few minutes after injection which is a unique behaviour as current bone cements require nearly 24 hours for complete curing. The tensile modulus of the hydrogel fillers is ~700 kPa, confirming the high strength in shear and bending of PNPHO-peptide hydrogels. The in vitro studies demonstrated complete bioresorption of these hydrogel fillers in 90 days. All these physicochemical characterisations along with the following bone specific in vitro and in vivo studies, confirmed that the invention can bring significant improvements in orthopaedic treatments.

PNPHO-Peptide Osteoconductive Properties

Figure 8:
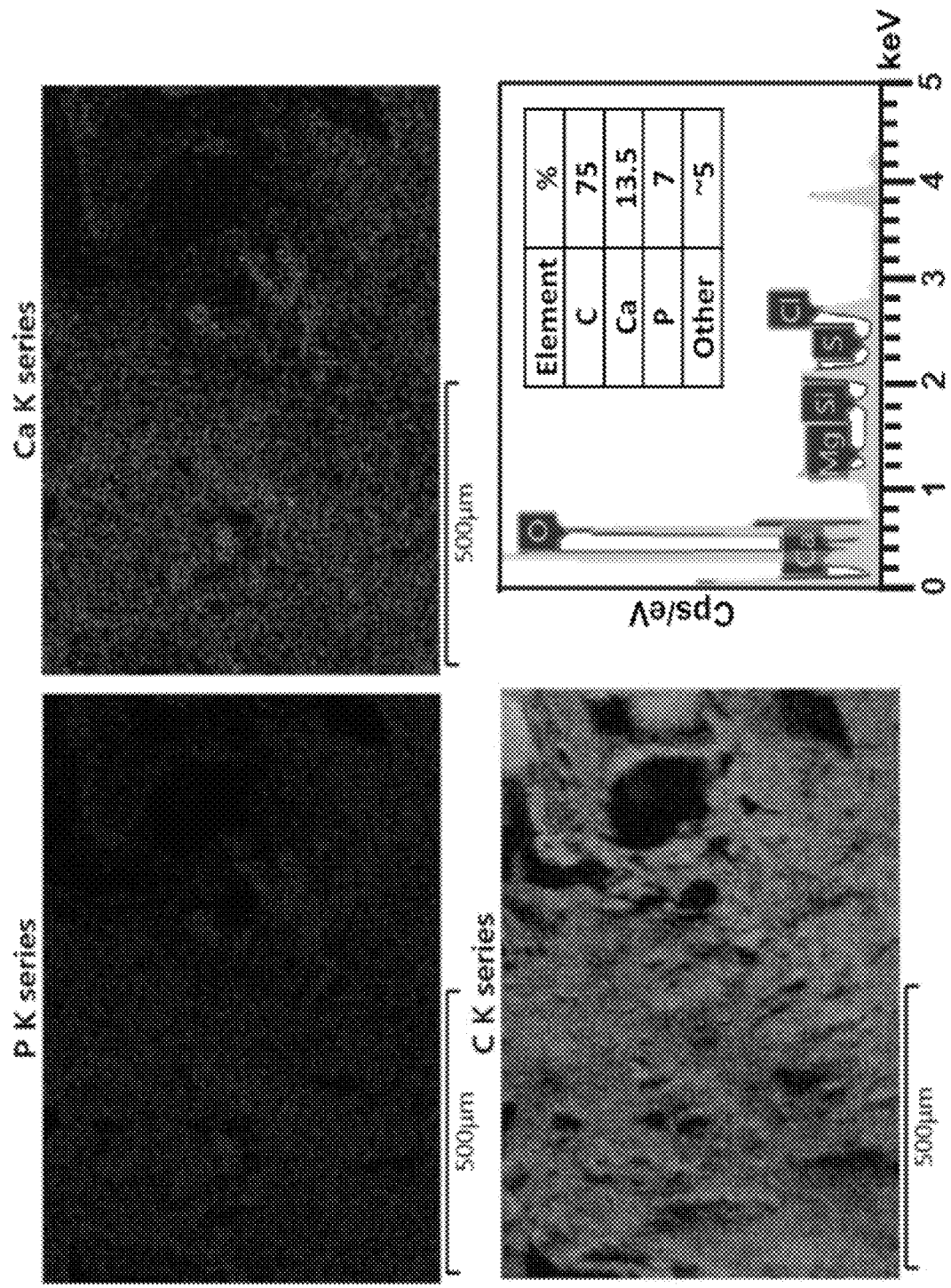
FIG. 8: The surface elemental analysis of PNPHO-NSPP hydrogels 14 days post-culture of osteoblast cells.
Figure 9A:
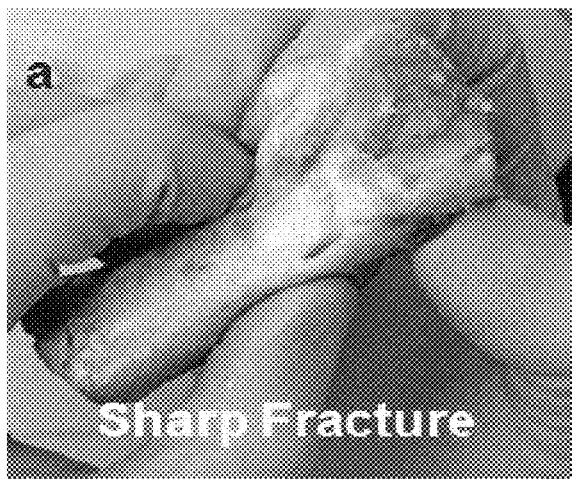
FIG. 9A-9D. Injection of PNPHO-NSPP injectable hydrogel to a sharp fracture zone (A and B) seal (C) and adhesion of the injectable hydrogel to the fracture zone (D).
Figure 9B:
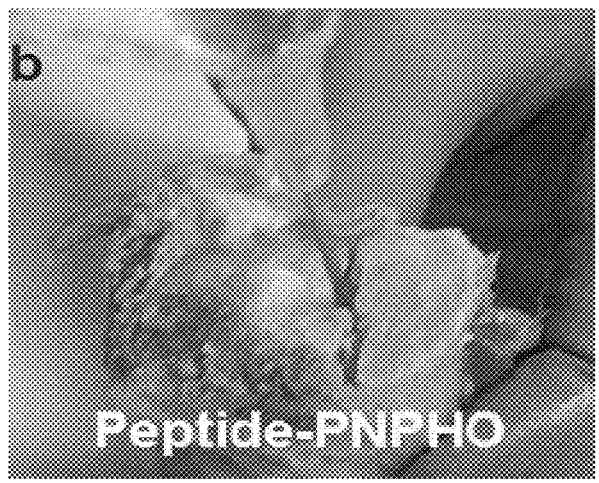
Figure 9C:
Figure 9D:
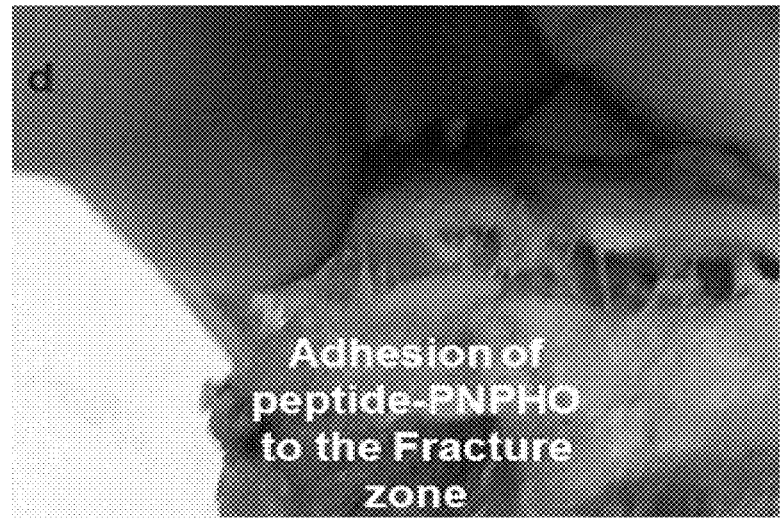

The results of the in vitro studies show the proliferation of near-surface interactive human pre-osteoblast cells on and within the PNPHO-peptide fillers. The numbers of osteoblast cells increased by 46.5±4.6% from day 1 to day 5 post-culture. The effect of extending the culturing time in order to deposit a mineralised extracellular matrix was then assessed. For this purpose, the well characterised osteoblast-like Saos-2 cell line was used as a model system. In vitro growth of these cells revealed that the amount of alkaline phosphatase (ALP) formation significantly increased. This was concluded as the absorbance of the ALP stained samples at 409 nm elevated from 0.3±0.4 after 7 days of culture to 0.41±0.2 from 15 days post-culture (FIG. 8). This result confirmed the osteoconductive properties of the PNPHO-peptide injectable hydrogels.

A detailed elemental analysis of the surface of PNPHO-peptide hydrogels after 14 days of culture in vitro with energy disperse X-ray scanning electron microscopy (FIG. 9) was conducted, which revealed deposited calcium and phosphate. The ratio of calcium to phosphate was 1.9, which is relatively close to that of the hydroxyapatite in natural bone extracellular matrix. These in vitro studies provided confidence that PNPHO-peptide has the capacity to support the growth; proliferation and mineralisation osteoblast-like cells and that they are osteoconductive.

PNPHO-Peptide Biomechanical Properties

An ex vivo clean sharp tibia fracture model was used to assess the biomechanical properties of the peptide-PNPHO hydrogels. The results of these ex vivo tests confirmed that the filler hydrogel can be injected and used to seal simple, clean fresh cadaver sheep tibia fractures—and the injected hydrogel thereafter adheres to the bone and fills the fracture, as shown in FIG. 9. This test was repeated for 6 independent tibia fractures, and the mechanical strengths of the bones were measured in each case. Surprisingly, an extraordinary 75%-90% of the strength of the bone was recovered following injection of the PNPHO-peptide solution. Control measurements were also performed and confirmed that this effect was due to the presence of both peptide and PNPHO polymer, since the mechanical performance was not restored in the absence of either compound.

The hydrogel polymers used in the invention settle within a few minutes at physiological conditions, e.g. temperature and pH, through a biologically benign lysine-reactive cross-linking reaction. Hence, the risk of necrosis classically seen with current bone repair solutions is eradicated or at the very least significantly reduced. In addition, these hydrogel fillers bioabsorb within two months and the rate of bioabsorption is compatible with the bone-remodelling rate due to the unique biomolecular structure of the hydrogel polymers disclosed herein. The results of in vivo studies in a subcutaneous mice model also, showed that the preferred polymerised used in the invention are highly cyto-compatible and upon the injection, these hydrogel fillers remain in situ without the need for any physical support. In addition, the subcutaneous injection of the preferred polymers disclosed herein in mice promotes the formation of blood vessels within and around the crosslinked polymer. In contrast with all current bone fillers, this angiogenic property of the preferred polymers for use with the invention would be expected to enhance the migration of osteogenic progenitor cells, increase the rate and quality of the regenerated bone, and thus should substantially shorten the osteoconductive period to generate viable, new bridging bone.

Animal Studies

Repair of Bone Fractures

PNPHO with the formulation of 8(5)/3/14/75 (PLA/HEMA(LA length)/OEGMA/NAS/NIPAAm mol %) was chemically bonded with thymosin β-4 (as a well-studied NSPP). In this specific formulation, 140 mg/ml of PNPHO was bonded with 30 mg/ml of thymosin β-4. The resulting conjugated system (PNPHO-thymosin) was used to study the potential of the technology to promote the healing rate of bone defects in vivo.

A sheep model study (n=20 animals) with 3 mm half radius tibia osteotomy (6 cm in diameter) was used. The study was carried out in Charles Sturt University, Wagga. The tests were conducted under the ethical approval of Animal Care and Ethics Committee number 13105. The tibial osteotomy was generated (shown in FIG. 10) with an oscillating saw. The injured bone site was internally immobilised with a standard 13 mm long, 4.5 mm bone plate and screws.

Figure 10:
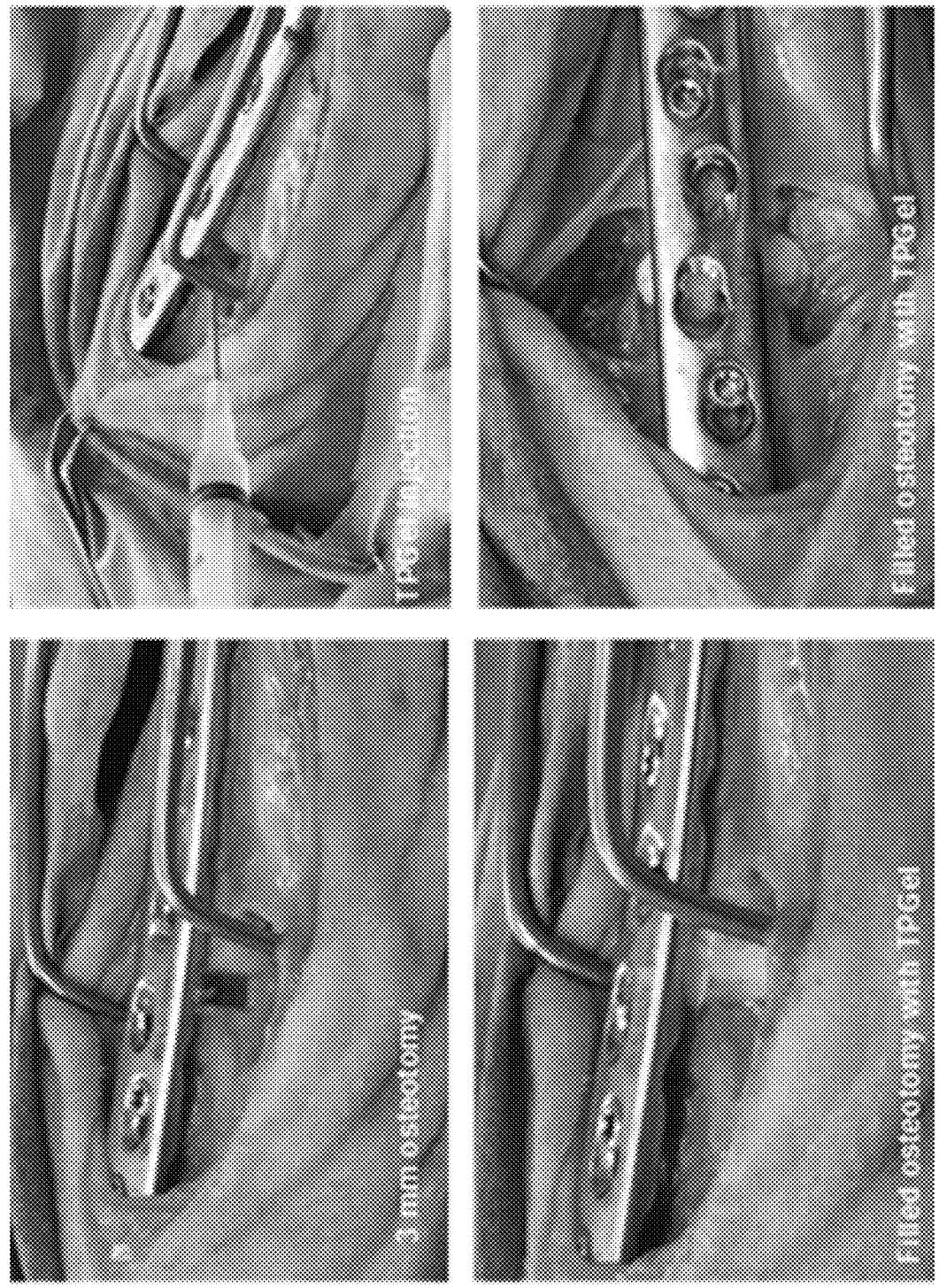
FIG. 10: Osteotomy formation and filling the gap with a temperature responsive hydrogel of PLA/HEMA(LA length)/OEGMA/NAS/NIPAAm polymer which is bonded to thymosin β-4conjugated, to promote the regeneration of bone formation.

The filter-sterilised PNPHO-thymosin was readily delivered to the defected site with 3 ml syringe through a 21 G needle, as shown in FIG. 10. The PNPHO-thymosin cross-linked in situ within few minutes post-injection (FIG. 10). The injected PNPHO-thymosin hydrogel retained at the injection site despite the presence of positive blood pressure at the osteotomy site.

After the surgery, in the test period of 8 weeks, the animal behaviour was monitored for signs of pain/distress, teeth grinding, foot stomping, lip curling, vocalisation, restlessness, depression, and lack of appetite. Heart and respiratory rates, body temperature, appetite, rumination and degree of lameness were also monitored. The animals maintained their well-being throughout the period of the study. All wounds healed favourably by secondary intention and with no scarring. Regular and comfort movements of the animals were also noticed in the housing facility. The observed behaviour of the animals suggests that the product is well tolerated as there were no obvious systemic reactions. Furthermore, no signs of local irritation at the trauma site were noticed.

In Vivo Effect of Hydrogel on Bone Osteotomy

The progress and extent of bone healing in animals, treated with PNPHO-thymosin hydrogels and the control groups was monitored. The bone healing progress with a PNPHO-thymosin injection was studied at different time points up to 8 weeks and it was compared with the natural bone healing process in exactly the same animal model in the literature and also with the negative control group (Marsell & Einhorn, 2011; Vetter et al., 2010).

Figure 11:
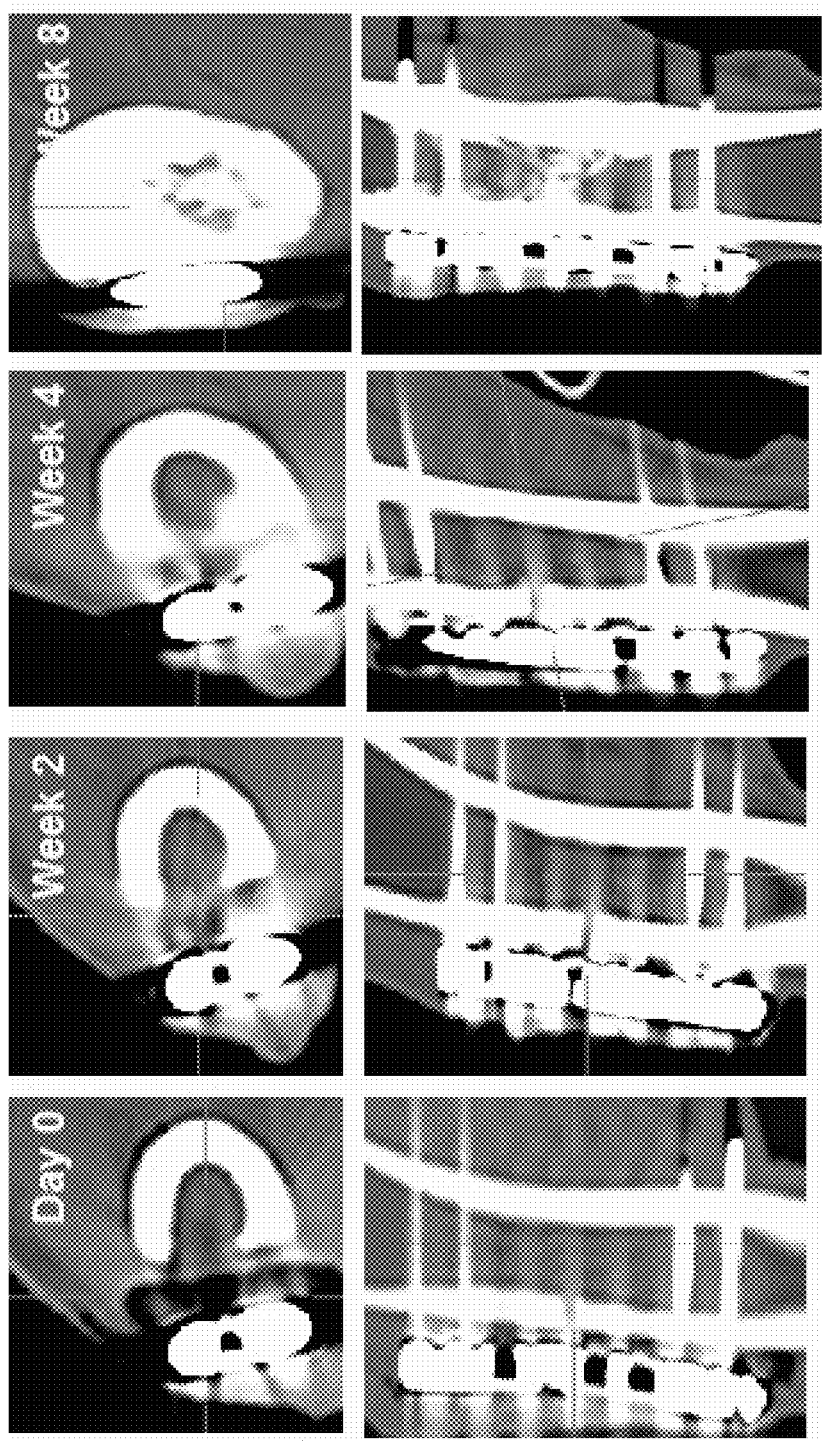
FIG. 11: CT scans of PNPHO-thymosin treated osteotomy sites at different time points.

The live animal CT scan after the surgery (FIG. 11) showed that the hydrogels retained and adhered to the bone surfaces at the injected site. After 4 weeks, the CT scan of the osteotomy site showed the formation of both endosteum and periosteum callus.

The CT number of the bone tissues was measured as an indication for the density of bone at different time points to confirm the regeneration of the bone at the osteotomy site. The assigned CT number for water is 0 and for compact bone is >1000. The CT number of the medullary cavity zone was increased four weeks post-surgery. This result showed that the ossification of the callus had begun by week 4 post-surgery, 3-4 weeks earlier than expected in the natural healing process. The ossification continued in PNPHO-thymosin treated osteotomies after 6 weeks and nearly complete bone formation was detected. In the literature, natural healing process of the sheep bone in 3 mm half radius osteotomy is comprehensively described. The summary of the findings in the literature is presented below. These findings highlight the advantageous properties of the polymer systems defined herein, to accelerate the bone-healing rate.

The reported progress of natural healing in the literature: In the natural healing process of a 3 mm half tibial sheep osteotomy model, during the first 7-14 days post-trauma, progenitor cells migrated to the site as a result of inflammation at the injured tissue. After 3-4 weeks post-surgery, vascular ingrowth and the formation of callus (a very soft collagen matrix) were detected. Subsequently, an osteoid (a gelatinous non-mineralised matrix comprised primarily of type I collagen) was secreted and the mineralisation of the generated matrix commenced 6 weeks post-trauma (Marsell & Einhorn, 2011; Vetter et al., 2010). After 7 weeks, the formation of a periosteal bony bridge between the proximal and distal parts of the osteotomy was observed. After 8 to 9 weeks post-trauma, the callus ossified, forming a bridge of woven bone between the fracture fragments. The whole bone remodelling phase is completed 3 to 6 months after the injury (Marsell & Einhorn, 2011; Vetter et al., 2010).

Short-Term Effect of PNPHO-Thymosin Treatment

Figure 12:
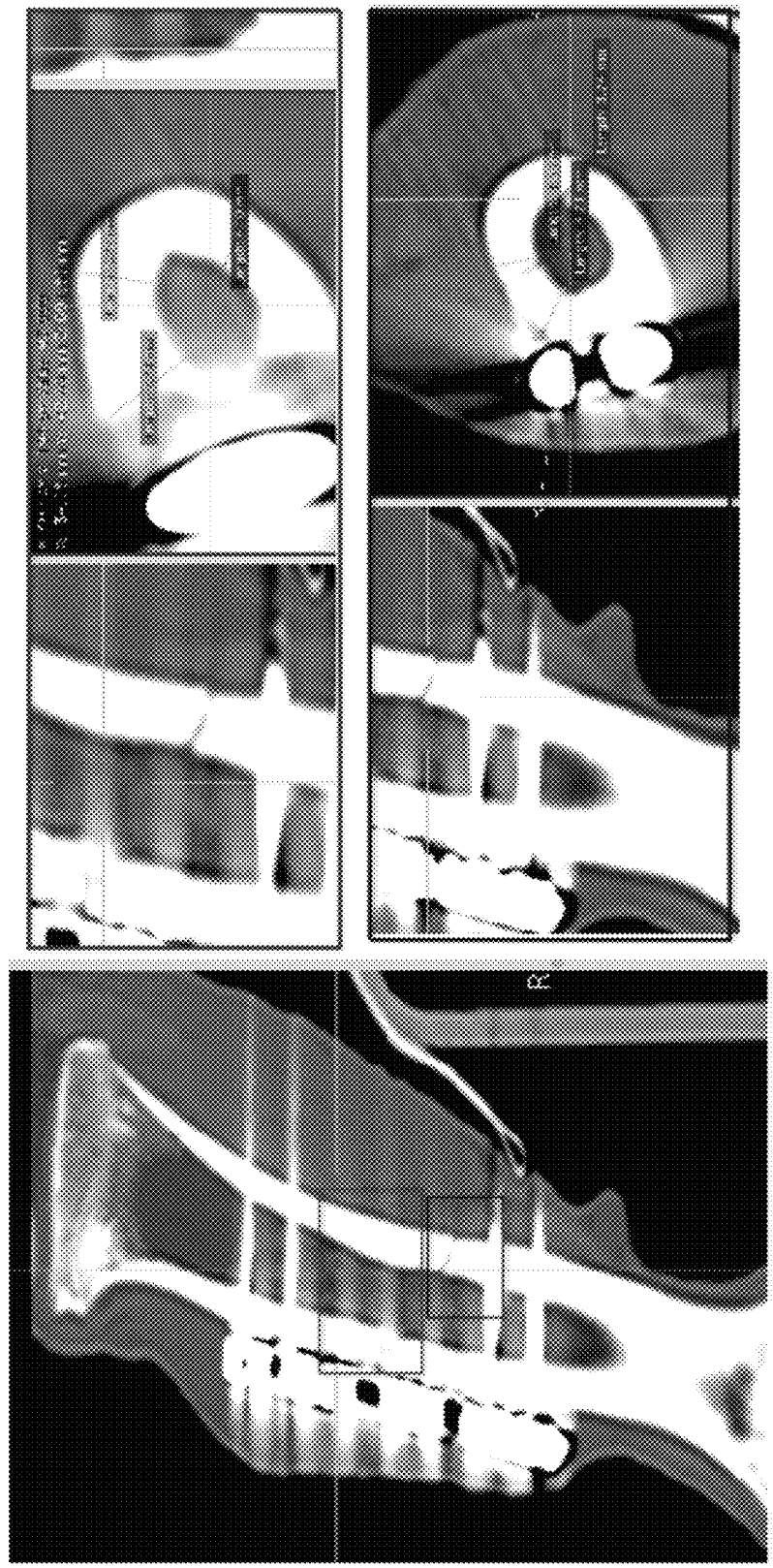
FIG. 12: The formation of bone at the osteotomy site 4 weeks after surgery and clear thickening of the bone at the tibial diaphyseal region in the PNPHO-thymosin treated samples at an osteotomy site.
Figure 13:
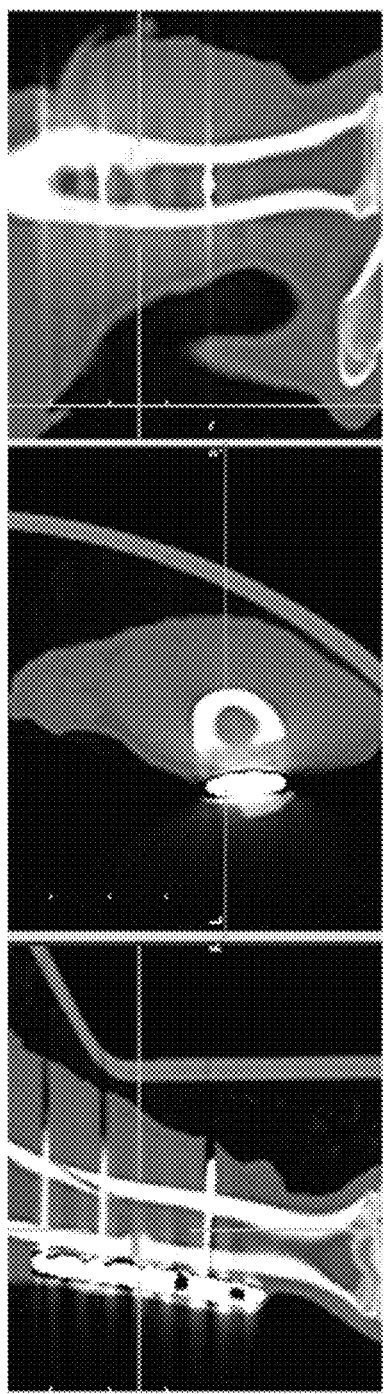
FIG. 13: Natural bone regeneration behaviour in a control group after 4 weeks.
Figure 13:
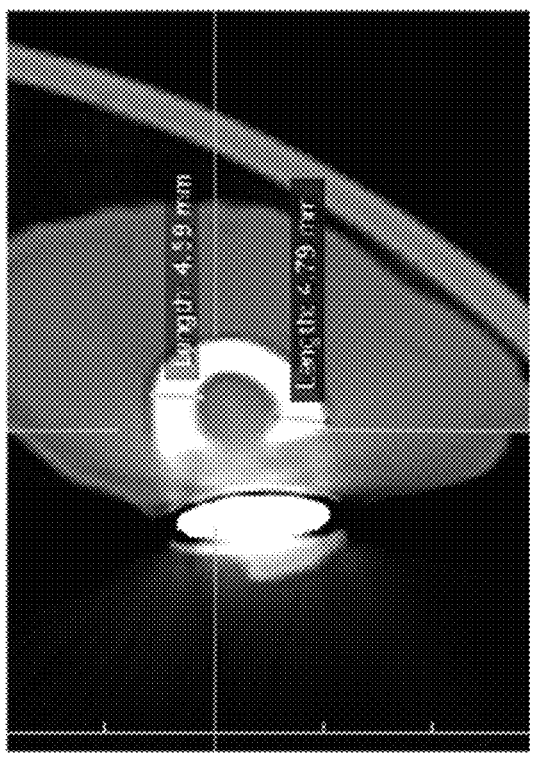

CT-scan results (FIG. 12) showed that the application of PNPHO-thymosin promoted the formation of endosteal bone even after 4 weeks. This effect resulted in thickening of the bone at the tibia diaphseal region and thus substantially strengthened the mechanical properties of the bone at the osteotomy site. In FIG. 13, the natural healing process of the bone defect after 4 weeks is shown. Direct comparison of the osteotomy sites in FIG. 12 and FIG. 13 confirmed that PNPHO-thymosin accelerates the formation of bone at the defected site compared with the control group.

Summary of Findings from Animal Studies

Based on the animal studies, the tested PNPHO-thymosin system was shown to promote the formation of bone even after 2 weeks of surgery. Both endosteal reparative bone and periosteal bone formation were noted in the bone regeneration studies conducted with PNPHO-thymosin treated samples. The results indicate that the injection of PNPHO-thymosin enhances the regeneration of dense arch bone at the bone marrow site to join the tibial diaphyseal segments is confirmed and that the formation of endosteal bone at the marrow site can substantially recover the strength of the bone.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method of treatment of a defect in a bone of a mammal, the method comprising introducing or administering a therapeutically effective amount of a polymer to said defect thereby to repair or restore said bone, the polymer comprising:
   a first monomer for binding water, wherein the first monomer is oligo (ethylene) glycol monomethyl ether methacrylate (OEGMA);
   a second monomer for imparting mechanical properties to said polymer, wherein the second monomer is hydroxyethyl methacrylate poly(lactic acid) (HEMA-PLA);
   a third monomer for binding to a natural or synthetic peptide or protein (NSPP), wherein the third monomer is N-acryloxysuccinimide (NAS); and
   a fourth monomer for imparting phase transition behaviour, wherein the fourth monomer is N-isopropylacrylamide (NIPAAm).

2. A method of treatment of a defect in a bone of a mammal, the method comprising introducing or administering a therapeutically effective amount of a composition that forms a hydrogel to said defect thereby to repair or restore said bone, the composition comprising:
   a natural or synthetic peptide or protein (NSPP); and
   a polymer;
   wherein the polymer includes:
   a first monomer for binding water, wherein the first monomer is oligo (ethylene) glycol monomethyl ether methacrylate (OEGMA);
   a second monomer for imparting mechanical properties to said polymer, wherein the second monomer is hydroxyethyl methacrylate poly(lactic acid) (HEMA-PLA);
   a third monomer that is bindable to said NSPP, wherein the third monomer is N-acryloxysuccinimide (NAS); and
   a fourth monomer for imparting phase transition behaviour, wherein the fourth monomer is N-isopropylacrylamide (NIPAAm),
   wherein the binding of said NSPP to the third monomer crosslinks the polymer, thereby enabling formation of said hydrogel when the composition is contacted with water.

3. A method of treatment of a defect in a bone of a mammal, the method comprising introducing or administering a therapeutically effective amount of a hydrogel to said defect thereby to repair or restore said bone, the hydrogel comprising:
   a natural or synthetic peptide or protein (NSPP); and
   a polymer;
   wherein the polymer includes:
   a first monomer for binding water, wherein the first monomer is oligo (ethylene) glycol monomethyl ether methacrylate (OEGMA);
   a second monomer for imparting mechanical properties to said polymer, wherein the second monomer is hydroxyethyl methacrylate poly(lactic acid) (HEMA-PLA);
   a third monomer that is bindable to said NSPP,
   wherein the binding of said NSPP to the third monomer crosslinks the polymer in the presence of water, and wherein the third monomer is N-acryloxysuccinimide (NAS); and
   a fourth monomer for imparting phase transition behaviour, wherein the fourth monomer is N-isopropylacrylamide (NIPAAm).

4. The method according to claim 1, wherein the NSPP is selected from one or more of the group consisting of collagen, fibrin, fibronectin, laminin (and isoforms thereof), bone morphogenic natural proteins, bone morphogenic synthetic proteins, and synthetic peptides, with the proviso that α-elastin, β-elastin, animal-derived elastin and/or tropoelastin in any form is not included.

5. The method according to claim 1, wherein the fourth monomer has a lower critical solution temperature (LCST) less than about 33° C.

6. The method according to claim 1, wherein OEGMA is in an amount of about 2-8 mol %, HEMA-PLA is in an amount of about 5-10 mol %, NAS is in an amount of about 14 mol % and NIPAAm is in an amount of about 79 mol %.

7. The method according to claim 2, wherein the NSPP is selected from one or more of the group consisting of collagen, fibrin, fibronectin, laminin (and isoforms thereof), bone morphogenic natural proteins, bone morphogenic synthetic proteins, and synthetic peptides, with the proviso that α-elastin, β-elastin, animal-derived elastin and/or tropoelastin in any form is not included.

8. The method according to claim 2, wherein the fourth monomer has a lower critical solution temperature (LCST) less than about 33° C.

9. The method according to claim 2, wherein OEGMA is in an amount of about 2-8 mol %, HEMA-PLA is in an amount of about 5-10 mol %, NAS is in an amount of about 14 mol % and NIPAAm is in an amount of about 79 mol %.

10. The method according to claim 3, wherein the NSPP is selected from one or more of the group consisting of collagen, fibrin, fibronectin, laminin (and isoforms thereof), bone morphogenic natural proteins, bone morphogenic synthetic proteins, and synthetic peptides, with the proviso that α-elastin, β-elastin, animal-derived elastin and/or tropoelastin in any form is not included.

11. The method according to claim 3, wherein the fourth monomer has a lower critical solution temperature (LCST) less than about 33° C.

12. The method according to claim 3, wherein OEGMA is in an amount of about 2-8 mol %, HEMA-PLA is in an amount of about 5-10 mol %, NAS is in an amount of about 14 mol % and NIPAAm is in an amount of about 79 mol %.

* * * * *